(12) United States Patent
Kim et al.

(10) Patent No.: US 12,329,850 B2
(45) Date of Patent: Jun. 17, 2025

(54) MICROALGAE HAVING HIGH LOLIOLIDE PRODUCTIVITY

(71) Applicant: KOREA RESEARCH INSTITUTE OF BIOSCIENCE AND BIOTECHNOLOGY, Daejeon (KR)

(72) Inventors: Hee Sik Kim, Daejeon (KR); Dae Hyun Cho, Daejeon (KR); Jin A Heo, Daejeon (KR); U Rim Kim, Daejeon (KR); Su Bin Park, Daejeon (KR)

(73) Assignee: KOREA RESEARCH INSTITUTE OF BIOSCIENCE AND BIOTECHNOLOGY (KR)

( * ) Notice: Subject to any disclaimer, the term of this patent is extended or adjusted under 35 U.S.C. 154(b) by 834 days.

(21) Appl. No.: 17/427,069

(22) PCT Filed: Jan. 31, 2020

(86) PCT No.: PCT/KR2020/001510
§ 371 (c)(1),
(2) Date: Jul. 29, 2021

(87) PCT Pub. No.: WO2020/159298
PCT Pub. Date: Aug. 6, 2020

(65) Prior Publication Data
US 2022/0387295 A1 Dec. 8, 2022

(30) Foreign Application Priority Data

Jan. 31, 2019 (KR) .................. 10-2019-0013108
Dec. 16, 2019 (KR) .................. 10-2019-0168315

(51) Int. Cl.
| | |
|---|---|
| A61K 8/9722 | (2017.01) |
| A61K 8/49 | (2006.01) |
| A61Q 19/08 | (2006.01) |
| C12N 1/12 | (2006.01) |
| C12P 17/08 | (2006.01) |
| C12R 1/89 | (2006.01) |

(52) U.S. Cl.
CPC .......... *A61K 8/9722* (2017.08); *A61K 8/4973* (2013.01); *A61Q 19/08* (2013.01); *C12N 1/125* (2021.05); *C12P 17/08* (2013.01); *C12R 2001/89* (2021.05)

(58) Field of Classification Search
None
See application file for complete search history.

(56) References Cited

U.S. PATENT DOCUMENTS

2013/0164322 A1 6/2013 Durvasula et al.

FOREIGN PATENT DOCUMENTS

| KR | 10-2012-0127685 A | 11/2012 |
|---|---|---|
| KR | 10-2014-0032201 A | 3/2014 |
| KR | 10-2015-0008238 A | 1/2015 |
| KR | 10-1805899 B1 | 1/2018 |
| KR | 10-2019-0116620 A | 10/2019 |

OTHER PUBLICATIONS

English translation of Kim (KR 101805899)—Jan. 10, 2018.*
Garrote (https://www.barnalab.com/en/blog/freeze-drying-microalgae-and-macroalgae/—accessed Feb. 2025).*
Office action dated Apr. 22, 2021 for corresponding Korean Patent Application No. 10-2019-0168316, including English translation, 7pp.
Office action dated Jan. 6, 2024 for corresponding Chinese Patent Application No. 202080012038.4, including English translation, 13pp.
Office action dated May 20, 2023 for corresponding Chinese Patent Application No. 202080012038.4, including English translation, 9pp.
Park, Sang Hee et al., "Loliolide Presents Antiapoptosis and Antiscratching Effects in Human Keratinocytes", Int. J. Mol. Sci. 2019, 20, 651, 17pp.
Park, Sang Hee et al., "Oxidative Stress-Protective and Anti-Melanogenic Effects of Loliolide and Ethanol Extract from Fresh Water Green Algae, Prasiola japonica", Int. J. Mol. Sci. 2018, 19, 2825, 15pp.
Yang, Hyo Hyun Yang et al., "Inhibitory effects of (–)-loliolide on cellular senescence in human dermal fibroblasts", Arch. Pharm. Res., Jul. 5, 2014, 9pp.
Heo, et al., "Characterization of a UV protecting compound from indigenous microalgal strain, Scenedesmus deserticola JD052," KMB2018 45th Annual meeting & international symposium, Jun. 27, 2018, Yeosu Expo Convention Center, Korea, p. 403, poster E-23. See poster E-23. "On Order".
Heo, et al., "Characterization of a UV protecting compound from indigenous microalgal strain, Scenedesmus deserticola JD052," KMB2018 45th Annual meeting & international symposium, Jun. 27, 2018, Yeosu Expo Convention Center, Korea, p. 403, poster E-23. See poster E-23.

* cited by examiner

*Primary Examiner* — Susan Hoffman
(74) *Attorney, Agent, or Firm* — Womble Bond Dickinson (US) LLP

(57) ABSTRACT

The present invention relates to novel microalgae with high productivity of loliolide, in which the *Scenedesmus* sp. HS4 of the present invention can be used as a biological resource to produce loliolide due to its high biomass productivity and high loliolide content, and can be used as a pharmaceutical composition or cosmetic composition which requires loliolide derived from *Scenedesmus* sp. HS4.

3 Claims, 17 Drawing Sheets
Specification includes a Sequence Listing.

MICROALGAE HAVING HIGH LOLIOLIDE PRODUCTIVITY

CROSS-REFERENCE TO RELATED APPLICATION(S)

This application is a U.S. National Phase Patent Application of PCT/KR2020/001510, filed Jan. 31, 2020, which claims priority to Korean Patent Application No. 10-2019-0013108, filed on Jan. 31, 2019, and Korean Patent Application No. 10-2019-0168315, filed on Dec. 16, 2019, the entire content of each of which is hereby incorporated by reference.

INCORPORATION BY REFERENCE

The instant application contains a Sequence Listing which has been submitted in ASCII format via EFS-Web and is hereby incorporated by reference in its entirety. Said ASCII copy, was created on Dec. 22, 2021, is named 209479-SEQLISTING.txt, and is 1,590 bytes in size.

TECHNICAL FIELD

Technical Field

The present invention relates to microalgae of *Senedesmus* sp. characterized by an excellent growth rate and a high content of loliolide.

Background Art

Since the skin is the outermost organ in the human body, it is inevitably and continuously affected by various air contaminants or physical stimuli, especially sunlight including ultraviolet (UV) rays, etc. and it is an organ more susceptible to damage because it is exposed to external stimuli compared to other organs. Cells constituting the skin by such external stimuli may experience a cellular aging phenomenon such as inhibition of cell growth and necrosis due to various causes, and the fibrous proteins present within the skin cells are destroyed or the amount of synthesis is reduced, thereby causing wrinkles.

The skin aging phenomenon may be classified into chronological aging (intrinsic aging), which is natural aging that occurs over time according to a biological process; a degenerative change that occurs in an area exposed to sunlight; and photoaging (actinic aging) in which the chronological aging occurs in a complex way. When the expression or activity of various factors related to cell growth is inhibited, natural cell aging may occur, and photoaging of the skin cells may be progressed by light with a wavelength of 280 nm to 400 nm included in the sunlight. Among them, damage to the skin or fibers may particularly occur by irradiation of ultraviolet rays such as UVB with a wavelength in the range of 280 nm to 320 nm, and a soot phenomenon that burns the skin black may occur. UVB irradiation promotes the accumulation of ROS and free radicals within skin cells, and it can induce oxidative stress on biomolecules such as DNA, proteins, and lipids by stimulating the intracellular signaling system by radicals, thereby causing damage to the skin tissue.

When the oxidative stress increases in skin cells, it stimulates keratinocytes of the epidermis or fibroblasts of the dermis and increases the expression of genes such as matrix metalloproteinase (MMP) and a collagen degrading enzyme through a series of intracellular signal transduction processes, and it induces a decrease in collagen, which accounts for 90% of the dermis and gives strength and tension to the skin and thus plays the role of protecting the skin from external stimuli or forces, thereby resulting in aging or formation of wrinkles of the skin. Therefore, it is possible to expect the effects of preventing aging of skin cells and improving wrinkles by regulating the expression of genes involved in the synthesis or degradation of fibrous proteins such as collagen.

The cell aging action according to the irradiation of UV rays contained in the sunlight can cause serious health problems because it not only causes problems due to damage to the skin from the cosmetic aspect, but also induce DNA damage in cells which can cause cancer or skin diseases. Therefore, a solution to solve these problems is necessary.

In relation to the above problems, as consumers' standard of living improves, consumers' concerns on the issues of skin aging and health are also increasing, studies to develop medicines or cosmetics to prevent and improve skin aging are actively undergoing, and attempts have been made to improve skin aging and wrinkles using extracts extracted from natural materials such as plants, and retinol (vitamin A), AHA (α-hydroxy acid), and adenosine are widely used as substances that contribute to skin regeneration by increasing the synthesis of collagen (a fibrous protein) and normalizing the keratinization process of the epidermis, however, these materials are known to have problems in that they are unstable to light and heat and have with skin irritation.

Meanwhile, loliolide is known as a substance synthesized mainly from plants or macroalgae. Loliolide was found in *Phyllanthus urinaria* and is known as a substance having the activity of inhibiting the penetration of hepatitis C virus (HCV). Loliolide has been reported as a substance having antioxidant activity in the marine macroalgae, *Sargassum ringgoldianum*. However, in freshwater microalgae, it is merely known that extracts contain loliolide, and there have been no reports with regard to attempts to synthesize a large amount of loliolide with high efficiency using freshwater microalgae as described above.

In addition, *Scenedesmus* sp. is classified as green algae, which belongs to the order Chlorophyta and the family Chlorophyceae according to the classification system, and they are present in 4-8 unit cells being attached together. *Senedesmus* is evenly distributed in freshwater all over the world, and it is known that the lipid content in the body is 20-30%. Although studies have been conducted on the conversion of lipids derived from *Senedesmus* into biodiesel, more studies are necessary for its use as a raw material for pharmaceuticals or cosmetics relating to skin beauty or skin health.

DISCLOSURE OF THE INVENTION

Technical Problem

An object of the present invention provides novel microalgae with excellent productivity, which can produce loliolide effective in prevention and improvement of skin aging, with higher efficiency compared to existing microalgae known in the art, by increasing the synthesis of fiber proteins in skin cells.

Additionally, an object of the present invention provides a pharmaceutical composition for preventing and improving skin aging using the novel microalgae extract described above.

Additionally, an object of the present invention provides a cosmetic composition for preventing and improving skin aging using the novel microalgae extract described above.

Technical Solution

To achieve the above objects, according to an aspect of the present invention, there is provided *Scenedesmus* sp. HS4 deposited under Accession No. KCTC 13784BP.

According to another aspect of the present invention, there is provided a pharmaceutical composition for preventing and improving skin aging, which contains an extract of *Scenedesmus* sp. HS4 deposited under Accession No. KCTC 13784BP or a fraction thereof as an active ingredient.

According to still another aspect of the present invention, there is provided a cosmetic composition for preventing and improving skin aging, which contains an extract of *Scenedesmus* sp. HS4 deposited under Accession No. KCTC 13784BP or a fraction thereof as an active ingredient.

According to still another aspect of the present invention, there is provided a composition for preventing and improving skin aging, which contains loliolide produced from *Scenedesmus* sp. HS4 deposited under Accession No. KCTC 13784BP.

Advantageous Effects

Since the *Scenedesmus* sp. HS4 newly improved in the present invention has characteristics in that it accumulates a high content of loliolide in cells and has excellent organic carbon catabolism efficiency, compared to other existing microalgae which are already reported, it can grow even in conditions where light is not provided and can be cultured at a rapid growth rate thereby being capable of securing high biomass productivity and loliolide productivity. Such high loliolide productivity provides the possibility of reducing the production cost of loliolide by culturing the microalgae of the present invention in large quantities, it is expected to be used in various medicines and cosmetics which have antioxidant and anti-aging effects.

However, the effects of the present invention are not limited to those effects described above, and other effects not described will be clearly understood by those skilled in the art from the following description.

MODE FOR CARRYING OUT THE INVENTION

Figure 1:
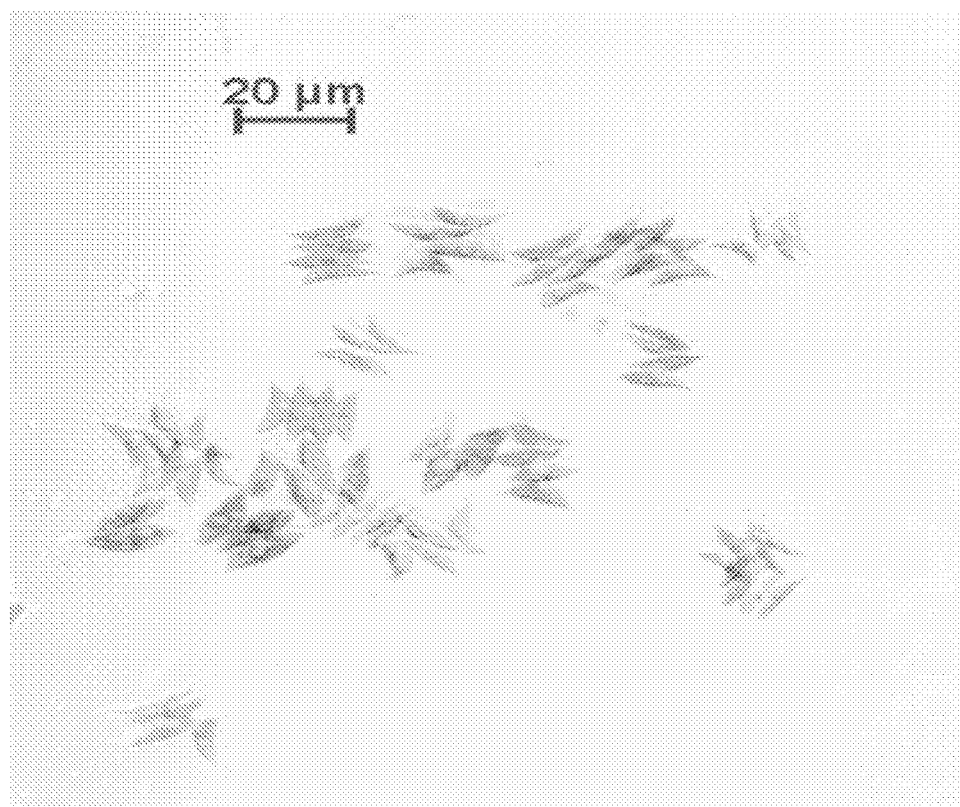
FIG. 1 shows a graph illustrating the *Scenedesmus* sp. HS4 of the present invention.

Hereinafter, the present application will be specifically described

1. Novel *Senedesmus* sp. Microalgae and Composition Containing the Same

The present invention provides microalgae which belong to a novel microalgae sp.

The novel microalgae of the present invention is *Scenedesmus* sp. HS4 deposited under Accession No. KCTC 13784BP.

The *Scenedesmus* sp. HS4 has the same nucleotide sequence as *Scenedesmus* sp. JD052 deposited under Accession No. KCTC 1899P as a result of 18s rRNA sequencing analysis, and considering the morphological characteristics of the cells, it was classified as belonging to a *Scenedesmus* sp. and was specifically named HS4.

Since efficiency of catabolism using organic carbon is maximized in the *Scenedesmus* sp. HS4, it shows a higher cell growth rate and thus has excellent biomass productivity compared to the photoautotrophic culture method, which is a common method of culturing microalgae when the *Scenedesmus* sp. HS4 is cultured in a culture medium containing glucose.

The *Scenedesmus* sp. HS4 can be cultured even in the absence of light. The *Scenedesmus* sp. HS4 is characterized in that even when the *Scenedesmus* sp. HS4 is cultured under heterotrophic culture conditions where light is excluded and only organic carbon is provided, it can grow at a growth rate similar to when it is cultured under mixotrophic culture conditions where both light and organic carbon are provided.

In particular, *Scenedesmus* sp. HS4 can produce loliolide in a very high content. *Scenedesmus* sp. HS4 can higher productivity of loliolide even compared to microalgae *Scenedesmus* sp. JD052 deposited under Accession No. KCTC 1899P. The microalgae *Scenedesmus* sp. JD052 is known to have higher productivity of loliolide compared to other types of microalgae. The microalgae *Scenedesmus* sp. HS4 of the present invention has significantly improved productivity of biomass and loliolide compared to both other known types of microalgae and JD052 microalgae. Therefore, by using the *Scenedesmus* sp. HS4 of the present invention, it is possible to replace the existing process or system which has been used for the production of loliolide.

In a specific embodiment of the present invention, *Scenedesmus* sp. HS4 was cultured under heterotrophic culture conditions in which only organic carbon (glucose) was provided and no light was given; cultured under mixotrophic culture conditions where both organic carbon and light were provided; and cultured under photoautotrophic culture conditions commonly used for culturing microalgae. As a result, it was found that the growth rate of *Scenedesmus* sp. HS4 was highest under the mixotrophic culture conditions, and the growth rate was also high under the heterotrophic culture conditions, and it was found that *Scenedesmus* sp. HS4 has the characteristic of being capable of growing even in the absence of light unlike common microalgae. Specifically, when *Scenedesmus* sp. HS4 microalgae is cultured in a medium containing 10 g/L of glucose as an organic carbon source and 1 g/L of yeast extract in the absence of light for 7 days, it can grow up to have a cell concentration of 5.9 g/L and can have biomass productivity of about 0.81 g/L/day. Therefore, considering the results that the cell concentration was about 5.65 g/L and the biomass productivity was about 0.91 g/L/day when the *Scenedesmus* sp. HS4 microalgae was irradiated with light in an amount of 50 $\mu mol \cdot m^{-2} \cdot s^{-1}$ and cultured for 7 days in a medium containing the same amount of glucose and yeast extract as described above, *Scenedesmus* sp. HS4 microalgae has the characteristic of being capable of growing even in the absence of light at a level similar to the case of culturing it under the condition where no light is given.

In addition, according to a specific embodiment of the present invention, when the *Scenedesmus* sp. HS4 microalgae and the *Scenedesmus* sp. JD052 microalgae were each cultured under the conditions as described above, it was found that the growth rate of HS4 cultured under the heterotrophic conditions and under the mixotrophic conditions was more excellent compared to the JD052 microalgae cultured under the photoautotrophic conditions, thus resulting in high productivity of biomass. As a result of examining their loliolide content, it was found that the loliolide productivity of was also about 2 to 4-fold higher compared to that of the existing JD052 microalgae.

Another aspect of the present invention provides a composition which includes the novel *Senedesmus* sp. microalgae.

The microalgae is *Scenedesmus* sp. HS4 which was deposited under Accession No. KCTC 13784BP.

The active ingredient included in the composition may not only be the *Scenedesmus* sp. HS4 deposited under Accession No. KCTC 13784BP, but also be a culture of the microalgae, a dried product of the culture solution, an extract of the culture, an extract of the microalgae, or a fraction of the extract.

The composition of the present invention containing *Scenedesmus* sp. HS4 may be prepared in a unit dose form by formulating with carriers, excipients and/or additives, or may be prepared by incorporating it into multi-dose containers according to a method that can be easily performed by those skilled in the art to which the present invention belongs. In particular, the composition may be in the form of a solution in oil or an aqueous medium, suspension, or emulsion, or may be in the form of an extract, powder, granule, tablet, capsule, gel (e.g., hydrogel) or lyophilisate. As the additive, a quasi-acid agent, a stabilizer, or a cryoprotectant may be used.

When the composition containing the *Scenedesmus* sp. HS4 is in the form of a lyophilisate, the composition includes lyophilizing the microalgae with a cryoprotectant and using the resultant in the form of powder, and the cryoprotectant may be natural sugar, skim milk powder, maltodextrin, dextrin, trehalose, maltose, lactose, mannitol, cyclodextrin, glycerol and/or honey, but the cryoprotectant is not limited thereto. In addition, the composition includes mixing the cryoprotectant with a preservation carrier, adsorbing, drying, and solidifying of the mixture for use, and the preservation carrier may be diatomaceous earth, activated carbon and/or defatted rice bran.

The composition containing the *Scenedesmus* sp. HS4 may be prepared by undergoing a step of mixing one or more selected from the microalgae, a culture of the microalgae, a concentrate of the culture, a dried product of the culture, an extract of the culture, an extract of the microalgae, and a fraction of the extract with any one of the carrier, excipient, or additive.

Descriptions of the strain, carrier, excipient, and additive are as described above. When a cryoprotectant is used as the additive, the composition containing the *Scenedesmus* sp. HS4 may be prepared in the form of powder by mixing the microalgae with a cryoprotectant, lyophilizing the mixture at −90° C. to −0° C., drying followed by pulverizing. Specifically, the lyophilization process may be a process of vacuum freezing for 65 to 75 hours under a temperature condition of −45° C. to −30° C. and a pressure condition of 5 mTorr to 50 mTorr, and the drying process may be performed under a temperature condition of 30° C. to 40° C.

2. Pharmaceutical Composition for Preventing and Improving Skin Aging

The present invention provides a pharmaceutical composition for preventing and improving skin aging. The pharmaceutical composition for preventing and improving skin aging according to one aspect of the present invention includes an extract of *Scenedesmus* sp. HS4 deposited under Accession No. KCTC 13784BP or a fraction thereof as an active ingredient.

In addition, the pharmaceutical composition for preventing and improving skin aging according to another aspect of the present invention may be one which includes loliolide as an active ingredient and may be one which is produced from *Scenedesmus* sp. HS4 deposited under Accession No. KCTC 13784BP.

The extract of *Scenedesmus* sp. HS4 may exhibit a useful effect in preventing and improving skin aging. The skin aging may be natural aging or photoaging of skin cells, and may be physiological and/or actinic aging (e.g., reduction of wrinkles, fine lines, skin elasticity and/or tension, etc.) of the skin that can be caused by skin aging, and it may be internal skin degradation in which the dermis becomes thinner due to exposure to UV rays, and particularly, external change of the skin due to aging (e.g., degradation of collagen fibers, etc.).

Since the extract of *Scenedesmus* sp. HS4 has the effect of inhibiting the aging of skin cells, in particular, it can improve skin wrinkles and increase skin elasticity to maintain good skin conditions in terms of beauty or skin health, can protect skin cells from UV rays, and can inhibit the negative effects on the skin caused by UV rays.

The extract of *Scenedesmus* sp. HS4 contains loliolide as an active ingredient. The loliolide is a substance which has antioxidant activity and thus has the effect of preventing or improving skin cell aging. Specifically, loliolide has the activity of improving skin wrinkles by increasing the amount of collagen by acting on skin cells, thereby promoting the expression of a collagen-synthesizing gene (e.g., Col1A1 gene), which is a kind of fiber protein constituting skin cells, and inhibiting the expression of a collagenase gene, which decomposes collagen (e.g., MMP1 gene). Additionally, loliolide can increase cell viability and increase the amount of collagen by improving phenomena (e.g., the decrease of viability of skin cells caused by UV rays or the decrease in the amount of collagen as described above), thereby capable of recovering the negative effects of UV rays on skin cells.

The loliolide may be contained in the composition at a concentration of 1 μg/mL to 25 μg/mL. Specifically, the loliolide may be contained in the composition at a concentration of 2 μg/mL to 23 μg/mL, 3 μg/mL to 20 μg/mL, 5 μg/mL to 18 μg/mL, 5 μg/mL to 15 μg/mL, or 5 μg/mL to 10 μg/mL. When loliolide is contained within the concentration described above based on the total composition, it has the effects of inhibiting the decrease of cell viability by UV rays without showing toxicity to the cells where the composition is treated, and increasing the amount of collagen production by effectively regulating the expression of collagen-associated genes.

In a specific embodiment of the present invention, the chemical structure of the active ingredient in the extract of the *Scenedesmus* sp. HS4 microalgae was analyzed via NMR spectroscopy including $^1$H NMR, $^{13}$C NMR, $^1$H-$^1$H COSY, HMQC and HMBC spectra, and it was confirmed that the extract of the present invention contains loliolide as an active ingredient by measuring the molecular weight of the active ingredient through the ESI-mass spectrum and comparing it with the existing database.

In a specific embodiment of the present invention, it was confirmed that loliolide shows no cytotoxicity to human dermal fibroblasts up to a concentration of 20 μg/mL and has an activity to recover the cell viability of the human dermal fibroblasts, which was reduced by irradiation with UV rays. In addition, it was confirmed that the loliolide treatment has the effects of promoting the expression of the collagen gene (Col1A1) and inhibiting the expression of the collagenase gene (MMP1).

The extract can be obtained by a method which includes culturing the *Scenedesmus* sp. HS4; drying the culture of the *Scenedesmus* sp. HS4 and obtaining a dried product thereof; and adding an organic solvent to the obtained dried product and extracting.

The step of culturing *Scenedesmus* sp. HS4 may be performed at a temperature condition of 20° C. to 30° C., in a medium consisting of glucose (5 g/L to 15 g/L) and an enzyme extract (0.5 g/L to 1.5 g/L), and under the condition with no light irradiation. In addition to the conditions above, the step of culturing may be performed under the condition where light is irradiated with a luminous intensity of 30 μmol·m$^{-2}$·s$^{-1}$ to 100 μmol·m$^{-2}$·s$^{-1}$. When the *Scenedesmus* sp. HS4 is cultured outside the above temperature range or in a range lower than the glucose concentration contained in the medium, the growth rate of is significantly reduced and thus the biomass being obtained may be reduced. Additionally, the amounts of substances that exhibit antioxidant and skin anti-aging effects (e.g., loliolide) may also be decreased, and thus there is a problem that the effects of anti-aging and improvement of skin cells may be significantly low even if the culture is extracted.

When the extract is obtained by extracting it from the raw material, examples of the extraction method may include a solvent extraction method and a reflux extraction method, for example, all known conventional extraction methods (e.g., ultrasonic extraction, filtration, etc.) may be used. The extraction process may be repeated several times, and thereafter, a step such as concentration or lyophilization may be additionally performed. Specifically, the obtained extract is concentrated under reduced pressure to obtain a concentrate, and after the lyophilization of the concentrate, a high concentration extract powder can be prepared using a pulverizer.

When the extract is obtained by extracting it from the raw material, the extraction process may be repeated several times, and thereafter, a method such as concentration or lyophilization may be additionally performed. Specifically, the obtained extract is concentrated under reduced pressure to obtain a concentrate, and after the lyophilization of the concentrate, a high concentration extract powder can be prepared using a pulverizer.

When extracting the extract, the solvent may be water, an organic solvent, or a mixture thereof. The organic solvent may be ethyl acetate, for example, alcohol, hexane (n-hexane), ether, glycerol, propylene glycol, butylene glycol, methyl acetate, dichloromethane, chloroform, or benzene, but the organic solvent is not limited thereto.

The extract of *Scenedesmus* sp. HS4 may be further fractionated, and the fraction obtained as described above may also be used as an active ingredient in a pharmaceutical composition of the present invention for preventing and improving skin aging.

In order to increase the content of loliolide, the extract of *Scenedesmus* sp. HS4 may be fractionated to obtain a *Scenedesmus* sp. HS4. The solvent that can be used in preparing the fraction may be an organic solvent (e.g., ethyl acetate, acetone, acetonitrile, chloroform, dichloromethane, ethyl ether, xylene, hexane, and a combination thereof, but the solvent is not limited thereto.

In addition, the fraction of the present invention may be obtained by further performing a conventional fractionation process in order to concentrate the loliolide content. For example, a fraction obtained by passing the extract of *Scenedesmus* sp. HS4 through an ultrafiltration membrane with a constant molecular weight cut-off value and an active fraction obtained through various purification methods additionally performed by separation by various kinds of chromatography (those designed for separation based on size, electric charge, hydrophobicity, or affinity), etc. are also included in the fraction of the present invention.

The active fraction is a fraction having a higher loliolide content separated from a fraction, and is also referred to as an active fraction or effective fraction. A specific active fraction having a higher loliolide content can be prepared by separation according to the properties of the active ingredients through gradient column chromatography, etc. among the fractions in which various components obtained through a conventional fractionation process (e.g., systemic fractionation) are mixed. As the column chromatography, a column chromatography may be performed using a filler selected from the group consisting of silica gel, sephadex, LH-20, ODS gel, RP-18, polyamide, toyopearl, and XAD resin and the column chromatography may be performed several times by selecting an appropriate filler as needed, but the column chromatography is not limited thereto. In using the chromatography, as for the elution solvent, elution rate, and elution time, a solvent, rate, or time commonly used in the art may be applied.

Meanwhile, the pharmaceutical composition including the extract or fraction thereof of the present invention as an active ingredient may be prepared in a unit dose form or may be prepared by incorporation into a multi-dose container by formulating the composition using a pharmaceutically acceptable carrier and/or excipient according to a method that can be easily performed by those skilled in the art to which the present invention belongs. In particular, the formulation may be in the form of a solution in oil or an aqueous medium, suspension, or emulsion or may be in the form of an extract, powder, granule, tablet, capsule, or gel (e.g., hydrogel) or lyophilisate, and a dispersing agent or stabilizing agent may additionally be included.

In addition, the extract or a fraction thereof included in the pharmaceutical composition can be delivered in a pharmaceutically acceptable carrier (e.g., colloidal suspensions, powders, saline, lipids, liposomes, microspheres, or nanospherical particles). These may form a complex or be associated with the vehicle, or may be delivered in vivo using a transport system known in the art (e.g., lipids, liposomes, microparticles, gold, nanoparticles, polymers, condensation reagents, polysaccharides, polyamino acids, dendrimers, saponins, adsorption enhancing substances, or fatty acids).

In addition to these, the pharmaceutically acceptable carrier may further include lactose, dextrose, sucrose, sorbitol, mannitol, starch, acacia, gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., commonly used in formulation, but the pharmaceutically acceptable carrier is not limited thereto. Besides, a lubricant, a wetting agent, a sweetening agent, a flavoring agent, an emulsifying agent, a suspending agent, a preservative, etc. may further be included in addition to the above components.

The pharmaceutical composition according to the present invention may be administered orally or parenterally during clinical administration, and may be used in the form of a common pharmaceutical formulation. That is, the pharmaceutical composition according to the present invention may be administered in various oral and parenteral dose forms during actual clinical administration, and it is prepared using a diluent or excipient (e.g., filler, extender, binder, wetting agent, disintegrant, surfactant, etc.) commonly used in the formulation. Solid preparations for oral administration include tablets, pills, powders, granules, capsules, etc., and such a solid preparation is prepared by mixing at least one excipient (e.g., starch, calcium carbonate, sucrose or lactose, gelatin, etc.) with an herbal extract or herbal fermented product. In addition to simple excipients, lubricants (e.g., magnesium stearate, talc, etc.) are also used. Liquid formulations for oral administration include suspensions, solutions for internal use, emulsions, syrups, etc., various excipients (e.g., wetting agents, sweetening agents, fragrances, preservatives, etc.) may be included, in addition to water and liquid paraffin, which are commonly used simple diluents. Formulations for parenteral administration include sterile aqueous solutions, non-aqueous solutions, suspensions, emulsions, lyophilized preparations, and suppositories. Non-aqueous solvents and suspensions may include propylene glycol, polyethylene glycol, vegetable oils (e.g., olive oil), and injectable esters (e.g., ethyl oleate), etc. As the base of the suppositories, Witepsol, Macrogol, Tween 61, cacao butter, laurin butter, glycerol, gelatin, etc. may be used.

The effective dose of the extract of the *Scenedesmus* sp. HS4 of the present invention or a fraction thereof may vary depending on factors such as a formulation method, administration method, patient's age, weight, sex, disease condition, food, administration time, administration route, excretion rate, and response sensitivity. It is generally 1 mg/day to 20 mg/day, preferably 5 mg/day to 10 mg/day, per kg of body weight of an adult patient. According to the judgment of a doctor or pharmacist, the extract of the *Scenedesmus* sp. HS4 of the present invention or a fraction thereof may be administered several times daily at regular time intervals, and preferably in divided doses 2 to 3 times daily.

The present invention provides a method for preventing, improving, or treating skin aging, which includes administering a composition including one or more selected from the group consisting of *Scenedesmus* sp. HS4 deposited under Accession No. KCTC 13784BP, a culture of the *Scenedesmus* sp. HS4, a concentrate of the culture, a dried product of the culture, an extract of the culture, and a fraction of the extract to a subject.

The subject may be a human or an animal excluding humans. When the subject has a good skin condition, the subject's skin aging can be prevented by administering the composition to a subject. In the case where the subject's skin aging has occurred, the subject's skin aging can be improved or treated by administering the pharmaceutical composition to the subject.

The prevention means reducing the risk of having a disease or disorder, and it means any action that inhibits or delays the onset of a disease by preventing the progression of one or more clinical symptoms of a disease in a subject who can be easily exposed to or susceptible to the disease, but who is not yet afflicted with or showing symptoms of the disease.

The treatment means reducing the risk of having a disease or disorder, and it means any action that improves or advantageously alters the symptoms of a disease by stopping or reducing the progression of the disease or one or more clinical symptoms thereof.

The improvement refers to any action that causes the symptoms of a disease or disorder to be improved or to be advantageous.

The composition, a formulation thereof, an administration method, dose, a concentration of the active ingredient contained in the composition, and the description of skin aging are as described above.

3. Cosmetic Composition for Preventing and Improving Skin Aging

The present invention provides a cosmetic composition for preventing and improving skin aging.

The cosmetic composition for preventing and improving skin aging according to an aspect of the present invention includes an extract of *Scenedesmus* sp. HS4 deposited under Accession No. KCTC 13784BP or a fraction thereof as an active ingredient.

In addition, the cosmetic composition for preventing and improving skin aging according to another aspect of the present invention may include loliolide as an active ingredient, and in particular, the loliolide may be one which is produced from *Scenedesmus* sp. HS4 deposited under Accession No. KCTC 13784BP.

The loliolide may be contained in the composition at a concentration of 1 μg/mL to 25 μg/mL. Specifically, the loliolide may be contained in the composition at a concentration of 2 μg/mL to 23 μg/mL, 3 μg/mL to 20 μg/mL, 5 μg/mL to 18 μg/mL, 5 μg/mL to 15 μg/mL, or 5 μg/mL to 10 μg/mL. When the loliolide is contained within the concentration described above based on the total composition, it has the effects of inhibiting the decrease of cell viability by UV rays without showing toxicity to the cells where the composition is treated, and increasing the amount of collagen production by effectively regulating the expression of collagen-associated genes.

The method of preparing the extract of *Scenedesmus* sp. HS4 or a fraction thereof is omitted because it is described in the method of "2. Pharmaceutical composition for preventing and improving skin aging".

The cosmetic composition of the present invention may include a cosmetically effective amount of the extract or a fraction thereof and a cosmetically acceptable carrier, in which the cosmetically effective amount refers to an amount sufficient to achieve the effects of preventing and improving skin aging.

The cosmetic composition of the present invention may further include other ingredients having a characteristic that can provide a synergistic effect on the activity of the extract or a fraction thereof within the range that does not affect the activities of preventing and improving skin aging of the extract or a fraction thereof. For example, the cosmetic composition may include adjuvants commonly used in cosmetic or dermatological fields (e.g., fatty substances, organic solvents, solubilizers, thickening and gelling agents, emollients, antioxidants, suspending agents, stabilizers, foaming agents, fragrances, surfactants, water, ionic or nonionic emulsifiers, fillers, metal ions sequestering and chelating agents, preservatives, vitamins, blocking agents, wetting agents, essential oils, dyes, pigments, perfumes, hydrophilic or lipophilic active agents, lipid vesicles, any other ingredients commonly used in cosmetics, etc.), and these ingredients may be included in an amount commonly used in cosmetics or dermatological fields.

The cosmetic composition of the present invention may be prepared in any formulation conventionally prepared in the art, and for example, it may be formulated as a cosmetic such as a solution, suspension, emulsion, gel, lotion, essence, cream, powder, soap, shampoo, conditioner, pack mask, surfactant-containing cleansing, cleansing foam, cleansing water, oil, liquid foundation, cream foundation, and spray.

When the formulation is a solution or emulsion, a solvent, solubilizer, or emulsifier may be used as a carrier component, and for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan may be used. When the formulation is a suspension, as a carrier component, liquid diluents (e.g., water, ethanol, or propylene glycol), suspending agents (e.g., ethoxylated isostearyl alcohol, polyoxyethylene sorbitol esters, and polyoxyethylene sorbitan esters, aluminum metahydroxide, microcrystalline cellulose, bentonite, agar, trakant, etc. may be used. When the formulation is a cream or gel, as a carrier component, wax, paraffin, trakant, animal oil, starch, cellulose derivatives, silicone, bentonite, polyethylene glycol, silica, zinc oxide, talc, etc. may be used. When the formulation is a powder or spray, as a carrier component, silica, talc, aluminum hydroxyl groups, lactose, calcium silicate, propellants (e.g., chlorofluorohydrocarbons, propane/butane, and dimethyl ether) may be used. When the formulation is a surfactant-containing cleansing, as a carrier component, aliphatic alcohol sulfate, aliphatic alcohol ether sulfate, sulfosuccinic acid monoester, imidazolinium derivative, isethionate, methyltaurate, sarcosinate, fatty acid amide ether sulfate, aliphatic alcohol, alkylamidobetaine, fatty acid glyceride, fatty acid diethanolamide, vegetable oil, lanolin derivative or ethoxylated glycerol fatty acid ester, etc. may be used.

4. Composition for Preventing and Improving Skin Aging

The present invention provides a composition for preventing and improving skin aging.

The composition for preventing and improving skin aging according to an aspect of the present invention includes loliolide produced from *Scenedesmus* sp. HS4 deposited under Accession No. KCTC 13784BP.

The description on the *Scenedesmus* sp. HS4 is omitted because it is as described in the method of "1. Novel *Scenedesmus* sp. microalgae".

The loliolide may be obtained by a method which includes a step of culturing the *Scenedesmus* sp. HS4; a step of obtaining a dried product by drying the culture of the cultured *Scenedesmus* sp. HS4; a step of extracting by adding an organic solvent to the obtained dried product; and a step of isolating loliolide from the extract. The descriptions on the culturing, drying, extraction steps, etc. are omitted because they are as described in "2. Pharmaceutical composition for preventing and improving skin aging".

The loliolide may be contained in the composition at a concentration of 1 μg/mL to 25 μg/mL. Specifically, the loliolide may be contained in the composition at a concentration of 2 μg/mL to 23 μg/mL, 3 μg/mL to 20 μg/mL, 5 μg/mL to 18 μg/mL, 5 μg/mL to 15 μg/mL, or 5 μg/mL to 10 μg/mL. When the loliolide is contained within the concentration described above based on the total composition, it has the effects of inhibiting the decrease of cell viability by UV rays without showing toxicity to the cells where the composition is treated, and increasing the amount of collagen production by effectively regulating the expression of collagen-associated genes.

In a specific embodiment of the present invention, it was confirmed that loliolide shows no cytotoxicity to human dermal fibroblasts up to a concentration of 20 μg/mL and has an activity to recover the cell viability of the human dermal fibroblasts, which was reduced by irradiation with UV rays. In addition, it was confirmed that the loliolide treatment has the effects of promoting the expression of the collagen gene (Col1A1) and inhibiting the expression of the collagenase gene (MMP1).

The extract of *Scenedesmus* sp. HS4 may exhibit a useful effect in preventing and improving skin aging. The skin aging may be natural aging or photoaging of skin cells, and may be physiological and/or actinic aging (e.g., reduction of wrinkles, fine lines, skin elasticity and/or tension, etc.) of the skin that can be caused by skin aging, and it may be internal skin degradation in which the dermis becomes thinner due to exposure to UV rays, and particularly, external change of the skin due to aging (e.g., degradation of collagen fibers, etc.).

Since the loliolide has the effect of inhibiting the aging of skin cells, in particular, it can improve skin wrinkles and increase skin elasticity to maintain good skin conditions in terms of beauty or skin health, can protect skin cells from UV rays, and can inhibit the negative effects on the skin caused by UV rays.

The composition may be used as a pharmaceutical composition or cosmetic composition. The descriptions on the composition are omitted because they are as described in "2. Pharmaceutical composition for preventing and improving skin aging" and "3. Cosmetic composition for preventing and improving skin aging".

The present invention provides a use of one or more selected from the group consisting of Scenedesmus sp. HS4 deposited under Accession No. KCTC 13784BP, a culture of the Scenedesmus sp. HS4, a concentrate of the culture, a dried product of the culture, an extract of the microalgae, an extract of the culture, and a fraction of the extract for the prevention, improvement, or treatment of skin aging.

The present invention provides Scenedesmus sp. HS4 deposited under Accession No. KCTC 13784BP, a culture of the Scenedesmus sp. HS4, a concentrate of the culture, a dried product of the culture, an extract of the culture, or a fraction of the extract, for use in prevention, improvement, or treatment of skin aging.

The present invention provides a use of one or more selected from the group consisting of Scenedesmus sp. HS4 deposited under Accession No. KCTC 13784BP, a culture of the Scenedesmus sp. HS4, a concentrate of the culture, a dried product of the culture, an extract of the microalgae, an extract of the culture, and a fraction of the extract for the preparation of a drug for prevention, improvement, or treatment of skin aging.

The descriptions on Scenedesmus sp. HS4 microalgae, a pharmaceutical composition including the same, a cosmetic composition including the same, skin aging, prevention, improvement, treatment, etc. are as described above.

Hereinafter, the present invention will be described in detail.

However, the following examples specifically illustrate the present invention, and the content of the present invention is not limited by the following examples.

[Example 1] Improvement of Scenedesmus sp. HS4 Microalgae

Figure 2:
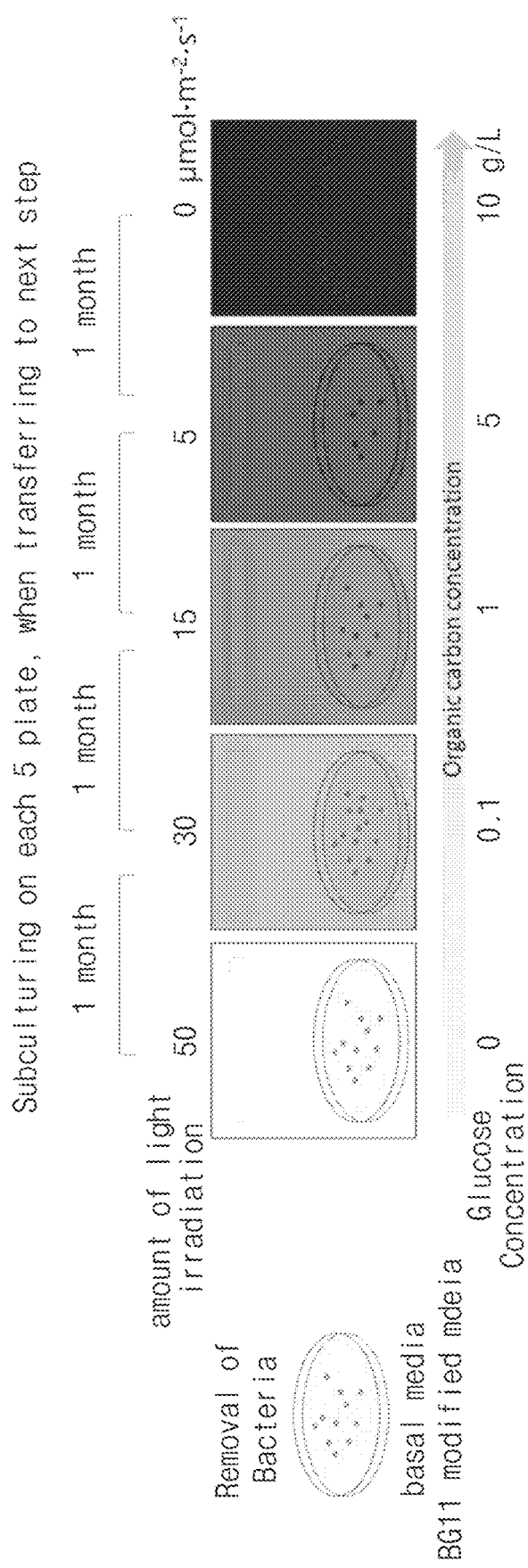
FIG. 2 shows a diagram illustrating the principle of the adaptive evolution induction process for improving the HS4 microalgae of *Senedesmus* sp. of the present invention, which relates to a method of culturing by gradually decreasing the amount of light irradiation and increasing the concentration of organic carbon in the medium while culturing the microalgae.

In order to prepare novel microalgae with high catabolism efficiency for organic carbon without being dependent on light, Scenedesmus sp. HS4 microalgae which was improved by inducing adaptive evolution for light sources and organic carbon was prepared. As the parent strain for the improvement, Scenedesmus sp. JD052 microalgae (Accession No. KCTC 1899P), which is one of the microalgae capable of producing loliolide, was used, and the Scenedesmus sp. JD052 was isolated from the water system of the clean area around Jeolla province (Korea). The Scenedesmus sp. JD052 was cultured by varying the concentration while providing organic carbon and varying the amount of light irradiation. In order to develop microalgae that can grow even in the absence of light, adaptive evolution was induced by a method in which the concentration of glucose in the medium is increased and the amount of light irradiation is gradually decreased, while culturing the microalgae in a conventional photoautotrophic culture medium for microalgae (see FIG. 2).

Specifically, the Scenedesmus sp. JD052 was cultured in a medium consisting of the composition shown in Table 1 below in which bacteria were removed. The medium was used by increasing the content of $K_2HPO_4$ from 0.04 g to 0.2 g in BG11 medium. The initial dose of light was set at 50 $\mu mol \cdot m^{-2} \cdot s^{-1}$, and the concentration of glucose was initially set at 0 g/L and cultured for one month; cultured for one month under the conditions where the light dose was 30 $\mu mol \cdot m^{-2} \cdot s^{-1}$ and the concentration of glucose was 0.1 g/L; cultured for one month under the conditions where the light dose was 15 $\mu mol \cdot m^{-2} \cdot s^{-1}$ and the concentration of glucose was 1 g/L; cultured for one month under the conditions where the light dose was 5 $\mu mol \cdot m^{-2} \cdot s^{-1}$ and the concentration of glucose was 5 g/L; and finally cultured for one month under the conditions where the light dose was 0 $\mu mol \cdot m^{-2} \cdot s^{-1}$ and the concentration of glucose was 10 g/L. The Scenedesmus sp. JD052 was cultured at a temperature of 25° C., and colonies with the fastest colony forming rate were selected on an agar plate every month under each condition described above, and novel microalgae which has excellent organic carbon catabolism and can grow even in the absence of light was obtained through the method of subculturing again on a plate under the next conditions.

As a sequencing analysis, it was found that the microalgae obtained through the above method has the same nucleotide sequence of 18s rRNA as the Scenedesmus sp. JD052, however, it showed a completely different characteristic by capable of growing only with organic carbon even in the absence of light, it was named novel Scenedesmus sp. HS4.

TABLE 1

| Composition of BG11 Modified Medium | | Content (g/L) |
|---|---|---|
| $NaNO_3$ | | 1.5 |
| $K_2HPO_4$ | | 0.2 |
| $MgSO_4 \cdot 7H_2O$ | | 0.075 |
| $CaCl_2 \cdot 2H_2O$ | | 0.036 |
| Citric acid | | 0.006 |
| Ferric ammonium citrate | | 0.006 |
| EDTA (disodium salt) | | 0.001 |
| $Na_2CO_3$ | | 0.02 |
| $NaNO_3$ | | 1.5 |
| Agar | | 10.0 |
| Trace Elements | $H_3BO_3$ | 0.00286 |
| | $MnCl_2 \cdot 4H_2O$ | 0.00181 |
| | $ZnSO_4 \cdot 7H_2O$ | 0.000222 |
| | $NaMoO_4 \cdot 2H_2O$ | 0.00039 |
| | $CuSO_4 \cdot 5H_2O$ | 0.000079 |
| | $Co(NO_3)_2 \cdot 6H_2O$ | 0.0000494 |

[Example 2] Confirmation of Growth Curve According to Culture Conditions

In order to confirm the growth pattern according to the culture conditions of the improved Scenedesmus sp. HS4 microalgae obtained Example 1 above, the Scenedesmus sp. HS4 was cultured under a heterotrophic culture condition where organic carbon was provided; cultured under a photoautotrophic culture condition where light was provided; and cultured under a mixotrophic culture condition where both organic carbon and light were provided, by varying the culturing conditions, respectively.

Specifically, first, in the case of the heterotrophic culture condition, 350 mL of a culture solution, in which glucose (10 g/L) and yeast extract (1 g/L) were added to a sterilized medium (pH 7.1) consisting of the composition of Table 1 above, the *Scenedesmus* sp. HS4 of the present invention was cultured in a 1 L flask at 25° C. for 7 days. The initial inoculation amount of the HS4 was set at 0.2 g/L. In the case of the photoautotrophic culture condition, other conditions were the same as the heterotrophic culture condition; however, a medium excluding glucose and a yeast extract was used and cultured by irradiating light with a light intensity of 50 $\mu mol \cdot m^{-2} \cdot s^{-1}$. In the case of the mixotrophic culture condition, the *Scenedesmus* sp. HS4 of the present invention was cultured under the same condition as the heterotrophic culture condition except that a light intensity of 50 $\mu mol \cdot m^{-2} \cdot s^{-1}$ was irradiated. During the culture process, the cell weight of the microalgae under each condition was measured every day.

Figure 3:
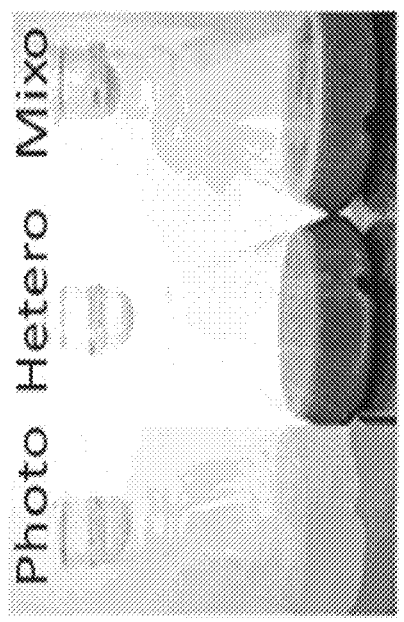
FIG. 3 shows a growth curve graph illustrating the HS4 microalgae of *Senedesmus* sp. of the present invention which was each cultured under light culture conditions ("Photo" of FIG. 3), subculture conditions ("Hetero" of FIG. 3), and mixed culture conditions ("Mixo" of FIG. 3) for 7 days, and an image of cultures.
Figure 3:
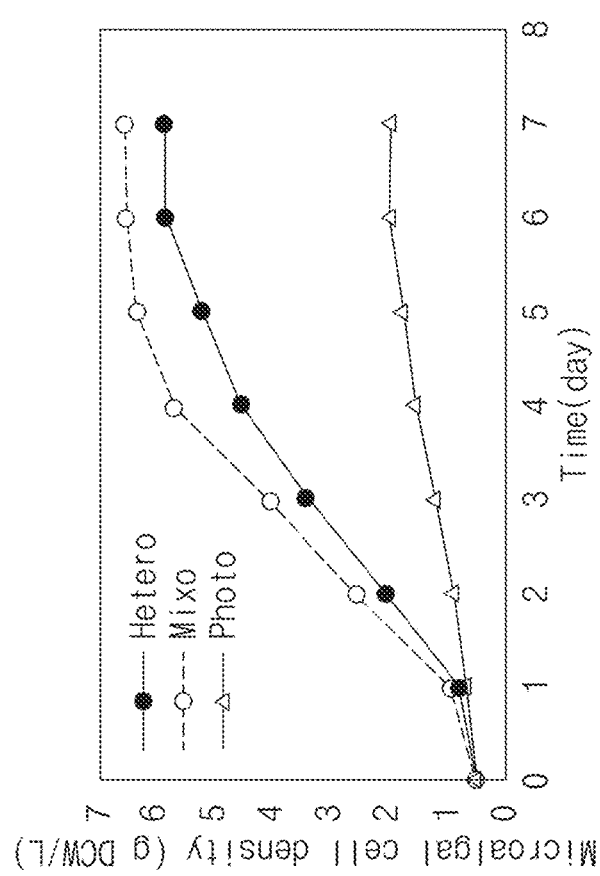
Figure 4A:
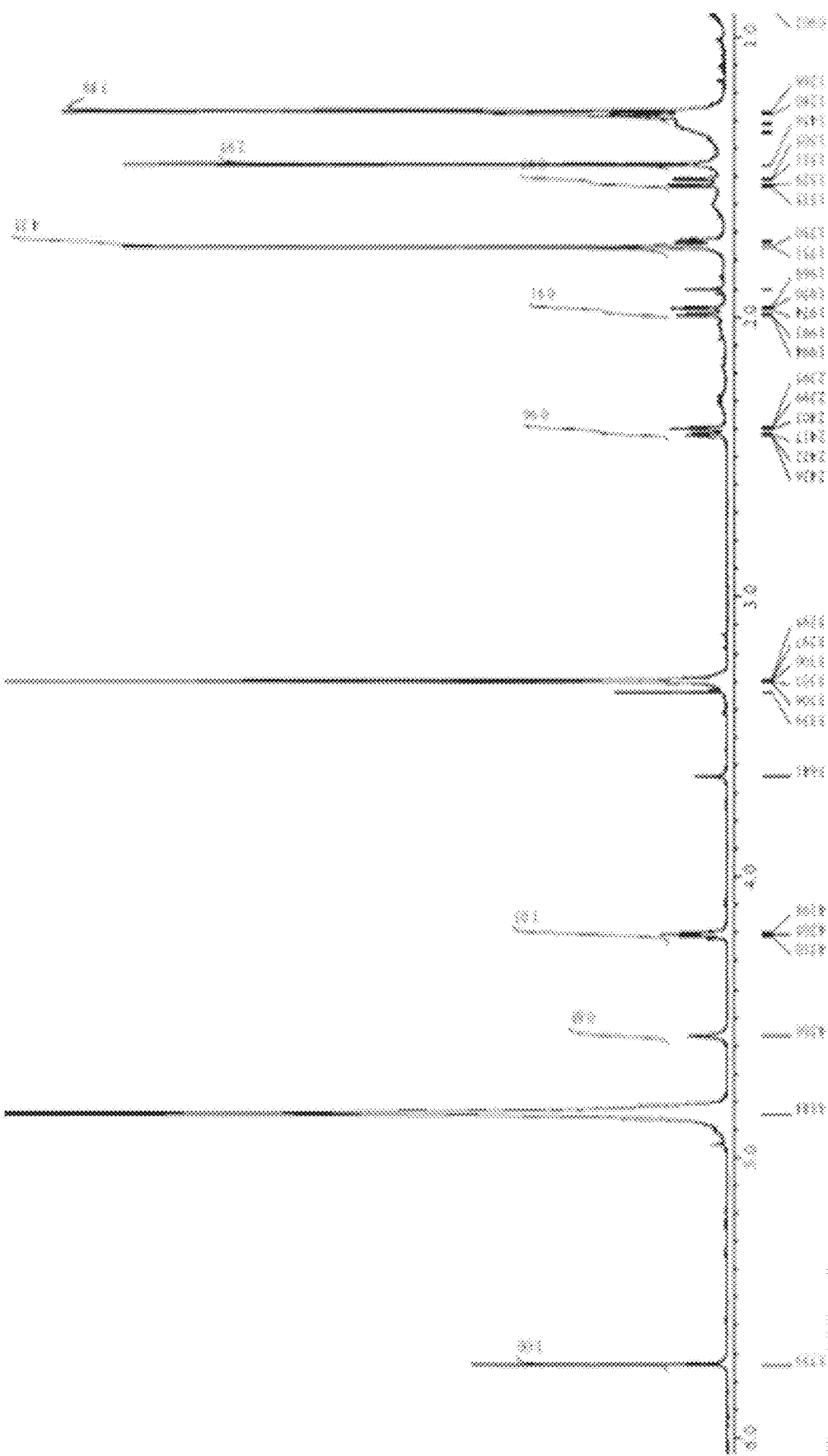
FIGS. 4*a* to 4*e* show the results of NMR spectroscopy to identify the chemical structure of the active ingredient in the HS4 microalgae extract of the *Senedesmus* sp. of the present invention in the order of $^1$H NMR, $^{13}$C NMR, $^1$H-$^1$H COSY, HMQC, and HMBC spectral measurement results, respectively.
Figure 4B:
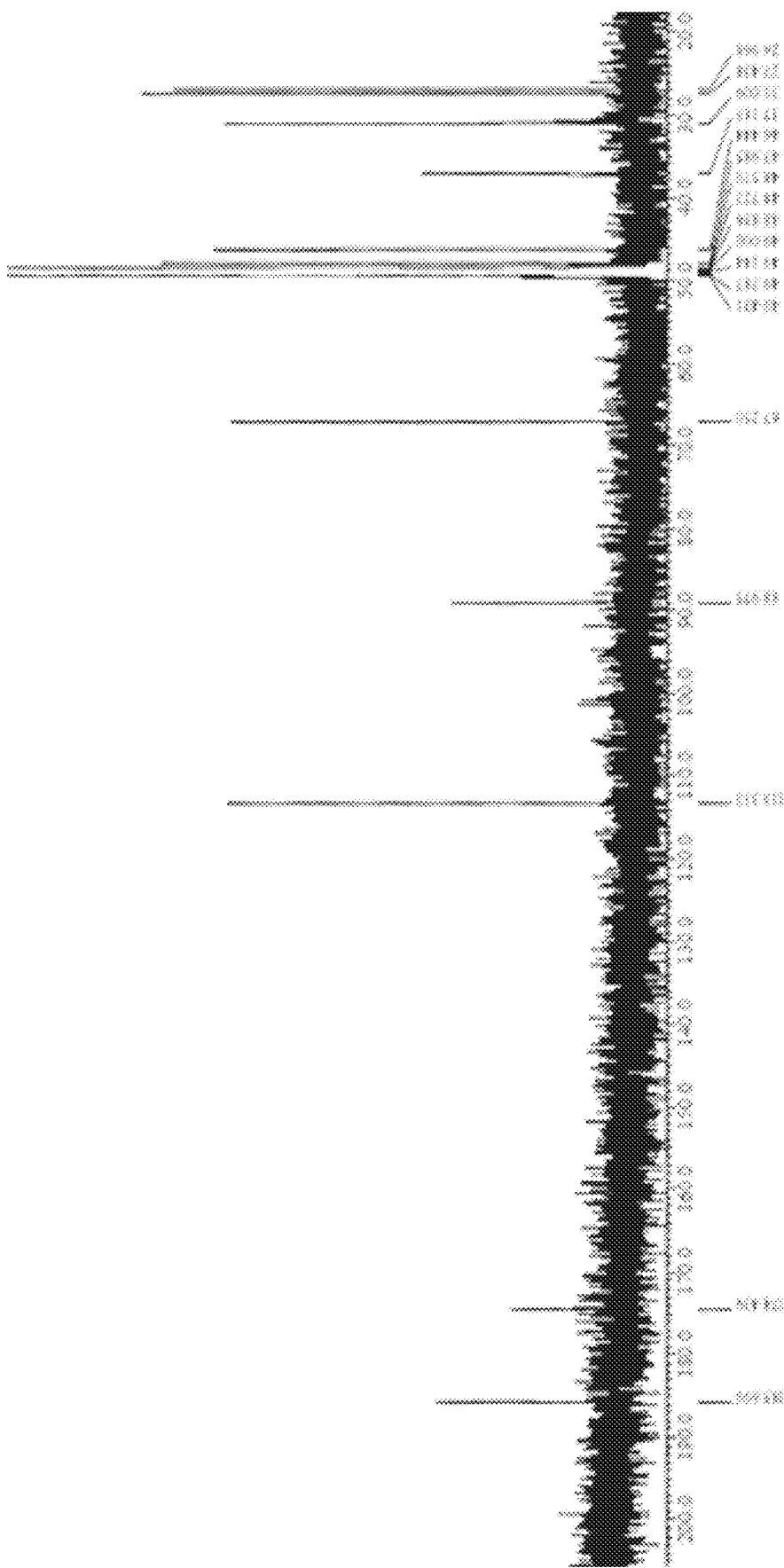
Figure 4C:
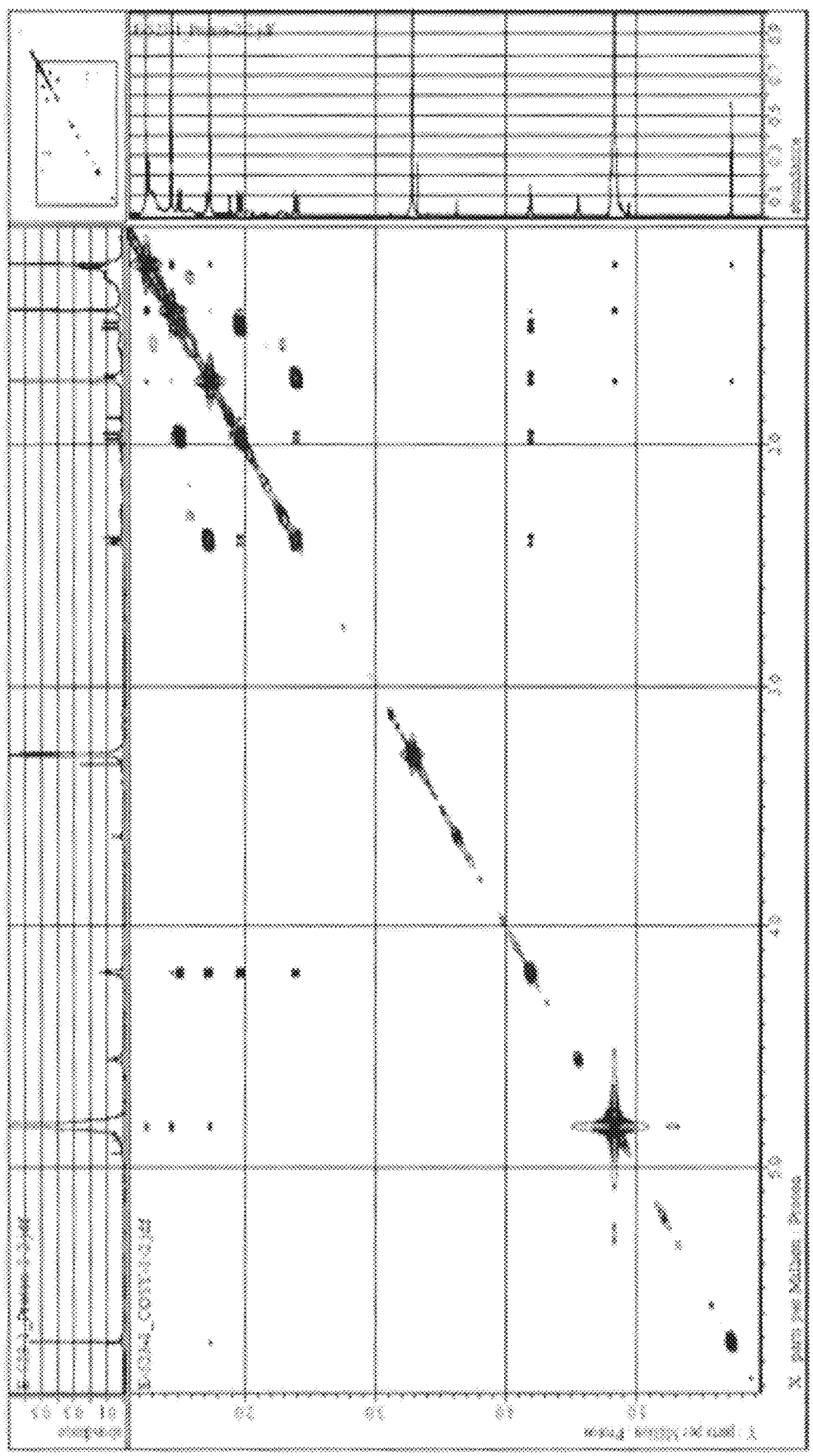
Figure 4D:
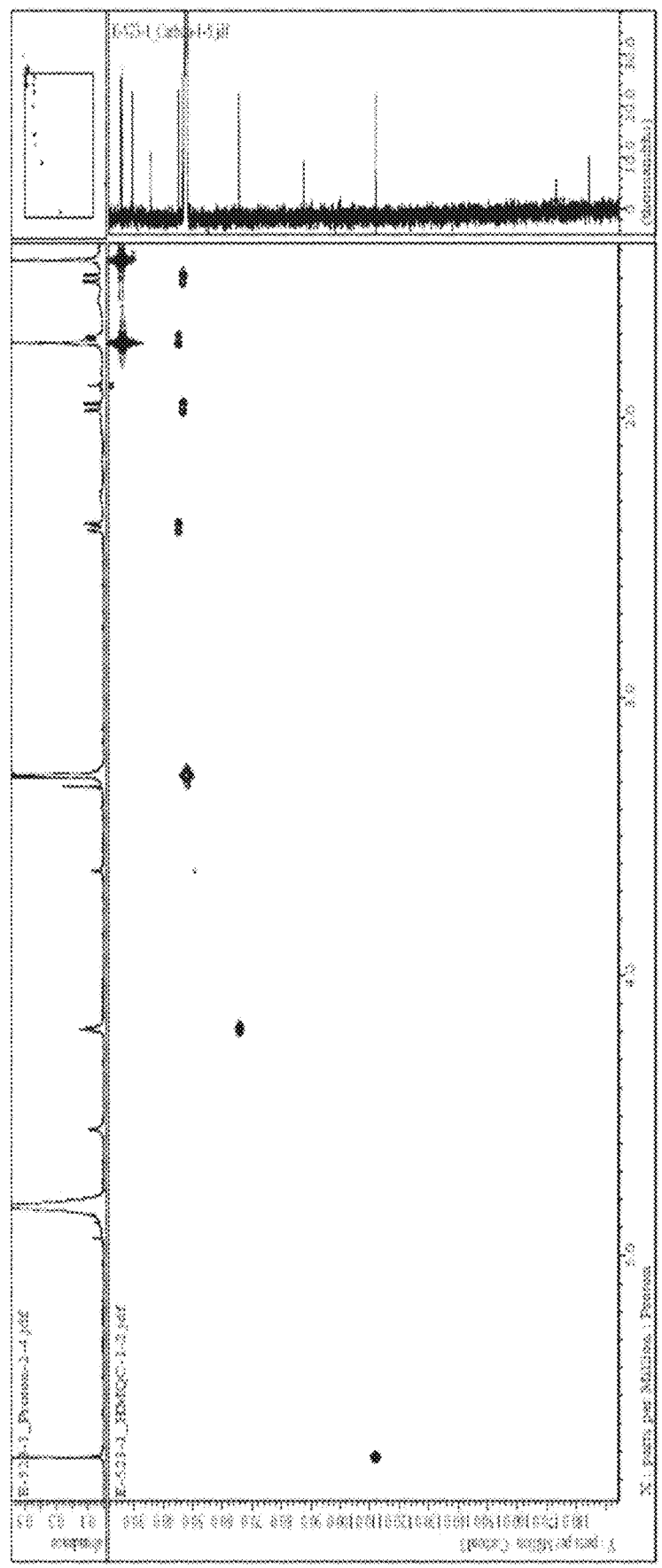
Figure 4E:
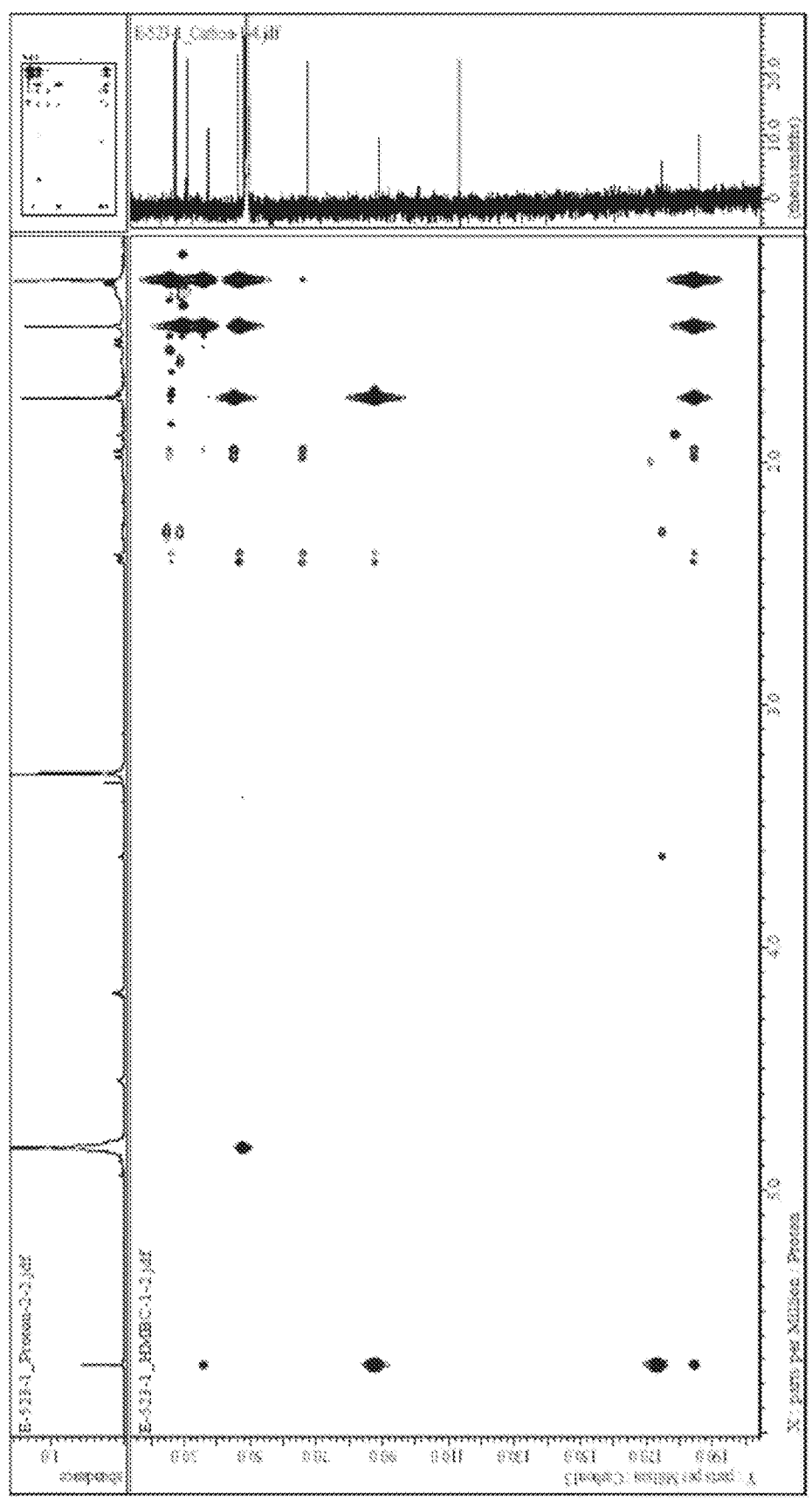

As a result, as shown in Table 2 below, the growth rate of the *Scenedesmus* sp. HS4 was the fastest under the mixotrophic culture condition where both light and organic carbon were provided. Even when the *Scenedesmus* sp. HS4 was cultured under the heterotrophic condition, it grew at a similar rate, although slower than that under the mixotrophic culture, and showed a significantly higher growth rate than that cultured under the photoautotrophic culture condition. After 7 days of culture, the final cell weight of the *Scenedesmus* sp. HS4 was 2.01 g/L when cultured under the photoautotrophic culture condition, 5.9 g/L when cultured under the heterotrophic culture condition, and 6.65 g/L when cultured under the mixotrophic culture condition, respectively. The daily average biomass productivity of the *Scenedesmus* sp. HS4 calculated accordingly was confirmed to be about 0.26 g/L/day when cultured under the photoautotrophic culture condition, about 0.81 g/L/day when cultured under the heterotrophic culture condition, and about 0.92 g/L/day when cultured under the mixotrophic culture condition, respectively. Accordingly, unlike other conventional microalgae or JD052 microalgae (which was the parent strain for improvement), the *Scenedesmus* sp. HS4 microalgae of the present invention grew with a high growth under the heterotrophic culture condition where no light was given and only organic carbon was provided, thus confirming that it can be cultured therein, and the growth rate was faster than that cultured under the photoautotrophic culture condition, thus confirming that a large amount of biomass could be produced (FIG. 3).

TABLE 2

| | Initial | Day 1 | Day 2 | Day 3 | Day 4 | Day 5 | Day 6 | Day 7 |
|---|---|---|---|---|---|---|---|---|
| Photoautotrophic Culture | 0.2 | 0.21 | 0.29 | 0.78 | 1.32 | 1.74 | 1.89 | 2.01 |
| Heterotrophic Culture | 0.2 | 0.34 | 0.99 | 1.56 | 2.21 | 3.56 | 5.32 | 5.9 |
| Mixotrophic Culture | 0.2 | 0.56 | 1.21 | 2.03 | 2.98 | 4.12 | 5.89 | 6.65 |

[Example 3] Analysis of Types of Active Ingredients

In order to determine what active ingredients are produced from *Scenedesmus* sp. HS4, 55 g of the extract was obtained from 1,000 g of the culture of the microalgae and the components thereof were analyzed. Through the process of centrifuging the cultured microalgae, the culture portion, which was the supernatant, was removed and only microalgal cells were obtained and lyophilized at −70° C. to remove moisture. Thereafter, cell extraction was performed from the lyophilized biomass using ethyl acetate, and after cell extraction, the organic solvent was distilled using a rotary vacuum evaporator to obtain an extract. The extract sample was dissolved in a solvent and fractions were fractioned by performing silica gel column chromatography and high performance liquid chromatography (HPLC). Among the fractions, the fractions showing activity were concentrated and purified through preparative ODS MPLC. The purified sample was dissolved in $CD_3OD$, and the chemical structure of the compound present in the extract was determined by measuring $^1H$ NMR, $^{13}C$ NMR, $^1H$-$^1H$ COSY, HMQC, and HMBC spectra.

As a result, the chemical structure of the substance contained in the sample of the *Scenedesmus* sp. HS4 extract was identified as loliolide. As a result of comparison with the NMR data of loliolide reported in the literature (Journal of the Korean Chemical Society, Vol. 48, No 4, 394-398, 2004), it could be determined that the active ingredient contained in the extract extracted from the microalgae of the present invention was (−)-loliolide (FIGS. 4a to 4e).

In addition, in order to further confirm the chemical structure of the active ingredient identified as described above, the molecular weight of the ingredient was measured by ESI-mass spectrum.

Figure 5A:
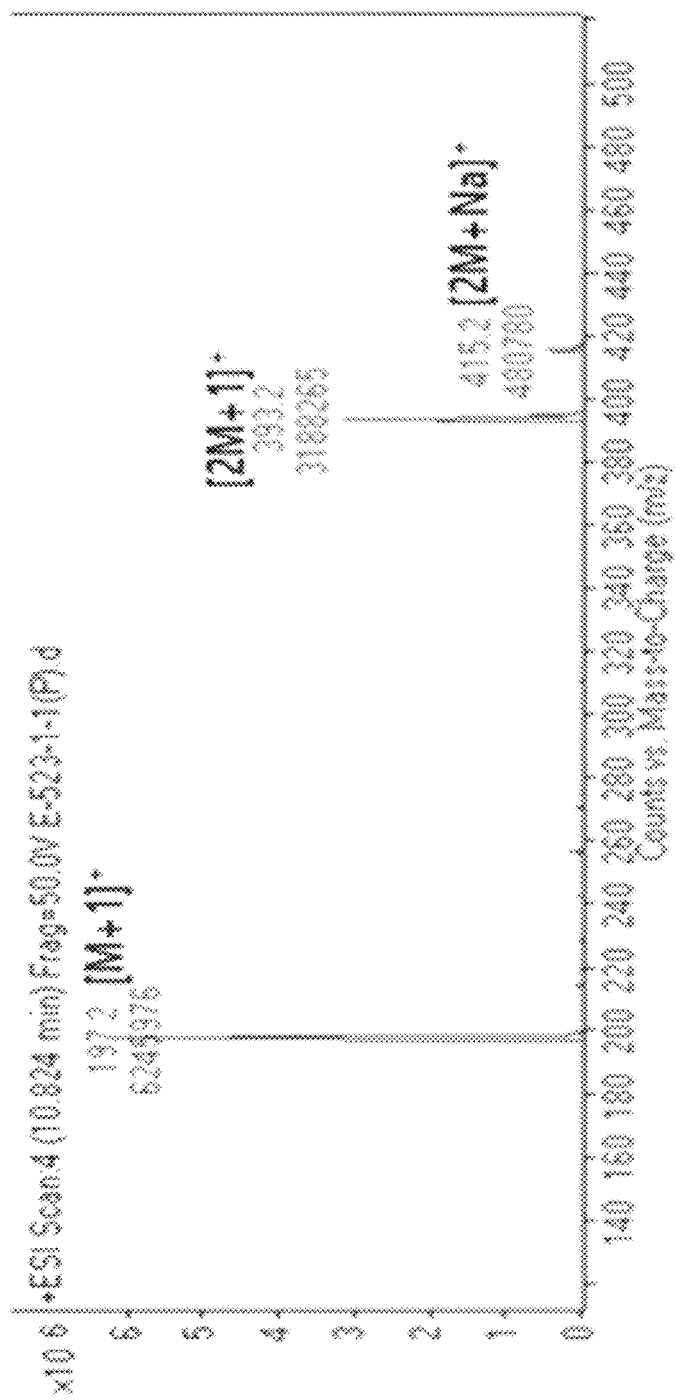
FIG. 5*a* shows the ESI-mass spectrum measurement results for measuring the molecular weight of the active ingredients in the HS4 microalgae extract of the *Senedesmus* sp. of the present invention.
Figure 5B:
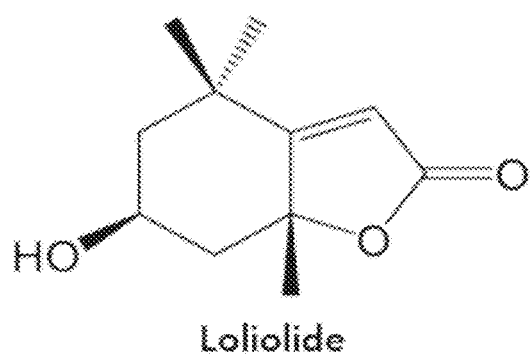
FIG. 5*b* shows a chemical structure of loliolide, an active ingredient in the HS4 microalgae extract of the *Senedesmus* sp. of the present invention, which was identified based on the results of FIGS. 4*a* to 4*e* and FIG. 5*a*.

As a result, peaks were observed at m/z 197.2 for $[M+H]^+$, m/z 393.2 for $[2M+H]^+$, and m/z 415.2 for $[2M+Na]^{++}$, confirming that the molecular weight is 196. Therefore, it was confirmed once again that the chemical structure analyzed by the result of NMR spectroscopic analysis was loliolide (FIGS. 5a and 5b).

[Example 4] Analysis of Loliolide Content

Figure 6A:
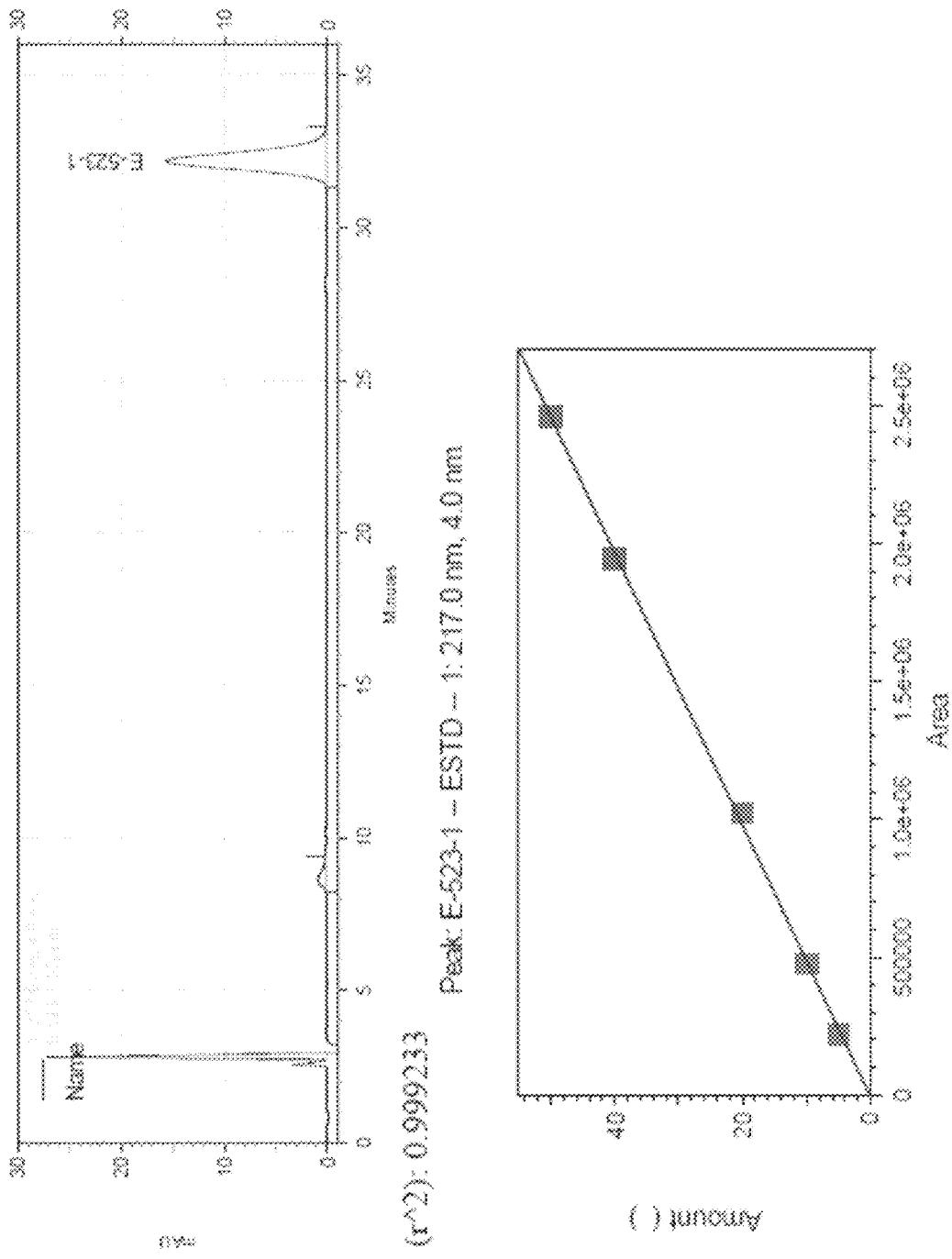
FIG. 6*a* shows an LC analysis result for purified loliolide and a quantitative line produced using the same.
Figure 6B:
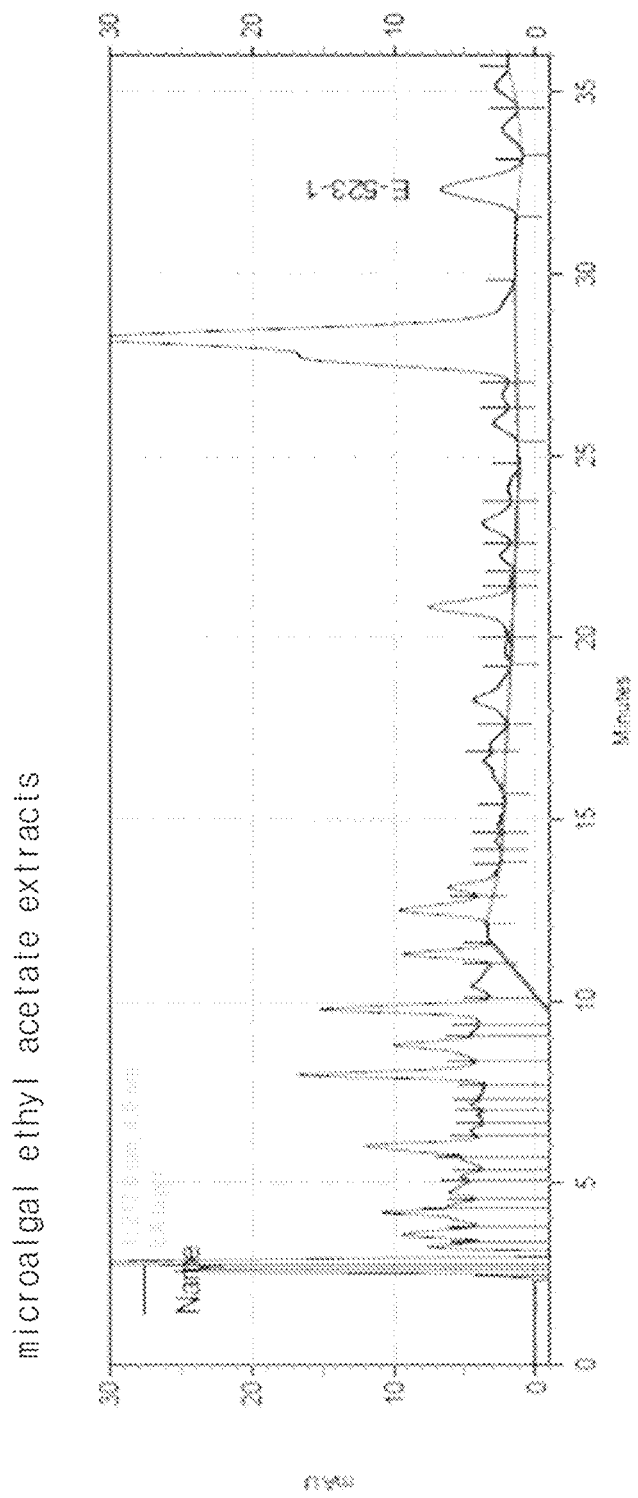
FIG. 6*b* shows an LC analysis result of the HS4 microalgae extract of the *Senedesmus* sp. of the present invention using the quantitative line of FIG. 6*a*.

Since the extract of *Scenedesmus* sp. HS4 contains loliolide as identified in Example 3, it was examined how much more *Scenedesmus* sp. HS4 could produce loliolide compared to other microalgae. First, a purified extract of loliolide was mixed with methanol to a concentration of 200 ppm, and the mixture was then diluted to prepare a quantitative line of loliolide (FIG. 6a). Thereafter, the extract of *Scenedesmus* sp. HS4 of the present invention obtained by extraction through the method same as in Example 3 and the extract of *Scenedesmus* sp. JD052 extracted by the same method were subjected to LC analysis, and the content of loliolide in the two microalgal extracts was analyzed through the quantitative line prepared above (FIG. 6b).

As a result, it was confirmed that 10,000 ppm of the ethyl acetate extract of *Scenedesmus* sp. HS4 of the present invention cultured by a mixotrophic culture contained 18.7 ppm of loliolide; and 10,000 ppm of the ethyl acetate extract of *Scenedesmus* sp. of the present invention cultured by a heterotrophic culture contained 14.3 ppm of loliolide. In comparison, it was confirmed that 10,000 ppm of the ethyl acetate extract of *Scenedesmus* sp. JD052 contained 17.6 ppm of loliolide.

In light of the above results, based on the extract at the same concentration, it was confirmed that the *Scenedesmus* sp. HS4 extract contained a similar level of content compared to the conventional JD052 microalgae extract.

[Example 5] Confirmation of Effect of Improving Loliolide Productivity by *Scenedesmus* sp. HS4

In order to confirm whether the loliolide productivity of *Scenedesmus* sp. HS4 microalgae is more improved compared to the conventional microalgae, the biomass productivity and the loliolide contained therein were compared for *Scenedesmus* sp. JD052 and *Scenedesmus* sp. HS4 microalgae.

First, since *Scenedesmus* sp. JD052 of corresponds to microalgae with very low efficiency of organic carbon catabolism, 350 mL of the sterilized culture (pH 7.1) consisting of the composition of Table 1 above was irradiated with a light amount of 50 $\mu mol \cdot m^{-2} \cdot s^{-1}$ in a 1 L flask at 25° C. and cultured for 7 days, and the initial inoculation amount of the JD052 was 0.2 g/L. The HS4 microalgae of the present invention were culture by a mixotrophic culture (where both light and organic carbon were provided) and by a heterotrophic culture (where only organic carbon was provided), respectively. Specifically, biomass productivity was confirmed by measuring the weight per biomass volume of each microalgae cultured as described above, and the loliolide productivity of each microalgae was confirmed using the loliolide content value in the microalgal extract analyzed in Example 5.

Specifically, first, in the case of heterotrophic culture conditions, other conditions were the same as those for culturing JD052, but a culture medium, to which 10 g/L of glucose and 1 g/L of yeast extract were added, was used and no light was irradiated. In the case of the mixotrophic culture conditions, in addition to the same conditions as in the case of the heterotrophic culture conditions, the culture was performed by irradiating light in a light amount of 50 $\mu mol \cdot m^{-2} \cdot s^{-1}$. The initial inoculation amount of the HS4 was 0.2 g/L.

Figure 7:
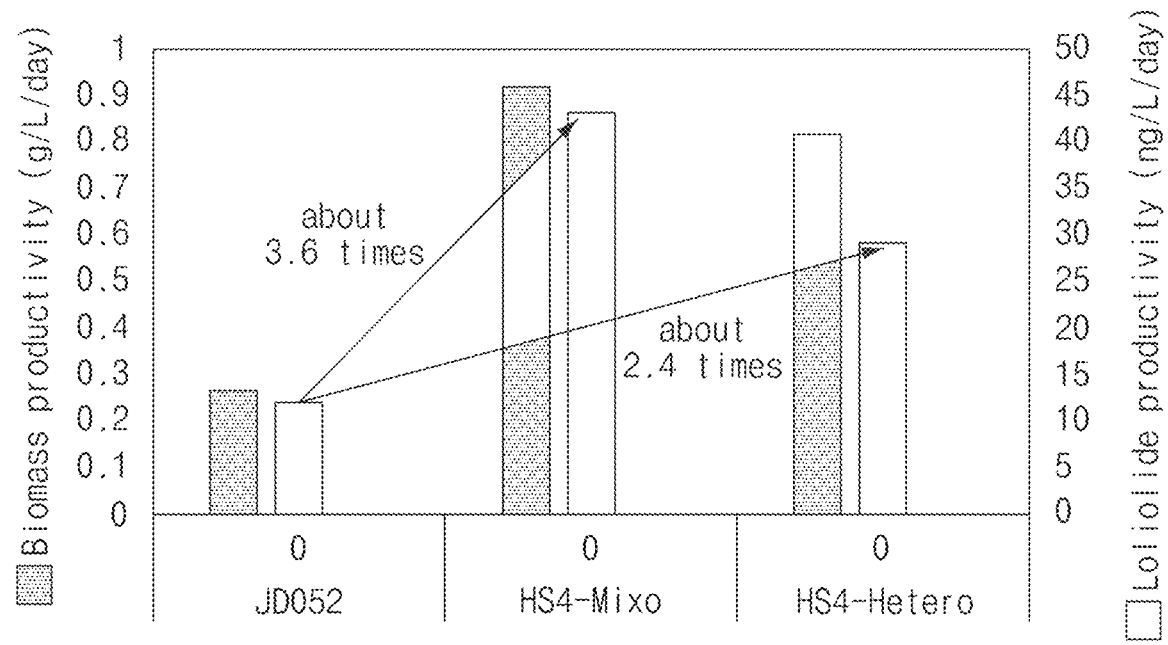
FIG. 7 shows a graph illustrating the results where the biomass production was compared between photocultured JD052 microalgae and the HS4 microalgae of the *Senedesmus* sp. of the present invention cultured under heteroculture (Hetero) and mixed culture (Mixo), and the content of loliolide in the extract of these microalgae was compared.

As a result, it was confirmed that in the case of *Scenedesmus* sp. JD052 cultured under the photoautotrophic culture conditions, the biomass productivity was 0.26 g/L/day and the loliolide productivity was 11.9 ng/L/day. In the case of *Scenedesmus* sp. HS4 of the present invention cultured under the heterotrophic culture conditions, it was confirmed that the biomass productivity was 0.81 g/L/day and the loliolide productivity was 28 ng/L/day. In the case of HS4 cultured under the mixotrophic culture conditions, it was confirmed that the biomass productivity was 0.92 g/L/day, and the loliolide productivity was 43 ng/L/day (FIG. 7).

In view of the above results, it was confirmed that the *Scenedesmus* sp. HS4 microalgae of the present invention biomass productivity was improved by about 3 times and 3.4 times and the loliolide productivity was improved by about 2.4 times and 3.6 times in the case of a heterotrophic culture conditions and a mixotrophic culture conditions, respectively, compared to the conventional JD052 microalgae. Therefore, the novel *Scenedesmus* sp. HS4 microalgae of the present invention showed an excellent growth rate compared to the conventional microalgae, even in culture conditions without light, and it was thus confirmed that the novel *Scenedesmus* sp. HS4 microalgae of the present invention has the characteristics with a remarkable increase in productivities of biomass and loliolide.

[Example 6] Confirmation of Cytotoxicity of Loliolide Produced from HS4 on Human Dermal Fibroblasts and Purified In order to confirm the effect of loliolide, which is the active ingredient produced from HS4, on the skin, the produced loliolide was purified and treated with human dermal fibroblasts (HDFs), and the effect thereof was confirmed.

The purification of loliolide was performed in the same manner as in Example 3, and an extract was obtained using ethyl acetate from a lyophilized culture of the *Scenedesmus* sp. HS4 microalgae of the present invention, and loliolide was purified through fractionation/concentration. In the case of culturing human dermal cells, human dermal fibroblasts purchased from Lonza (Basel, Switzerland) were cultured in a 5% $CO_2$ cell incubator at 37° C. using a medium in which 10% fetal bovine serum (FBS, 51480, Biowest, France) was further added to Dulbecco's modified Eagle's medium (DMEM medium, L0103-500, Biowest, France).

First, whether loliolide has cytotoxicity against human dermal fibroblasts was confirmed through WST-1 assay. After dispensing the cultured human dermal fibroblasts into a 96-well plate at $4 \times 10^3$ cells/well and culturing for 24 hours, the loliolide purified from *Scenedesmus* sp. HS4 microalgae was treated at concentrations of 0 μg/mL, 2 μg/mL, 5 μg/mL, 10 μg/mL, and 20 μg/mL, respectively. After 24 hours have elapsed after the loliolide treatment, the solution was treated in the medium using a WST-1 assay kit (EZ-cytox cell viability kit, Itshio, Korea), the absorbance was measured at a wavelength of 450 nm with a microplate reader (iMark microplate reader, Bio-Rad, USA).

Figure 8:
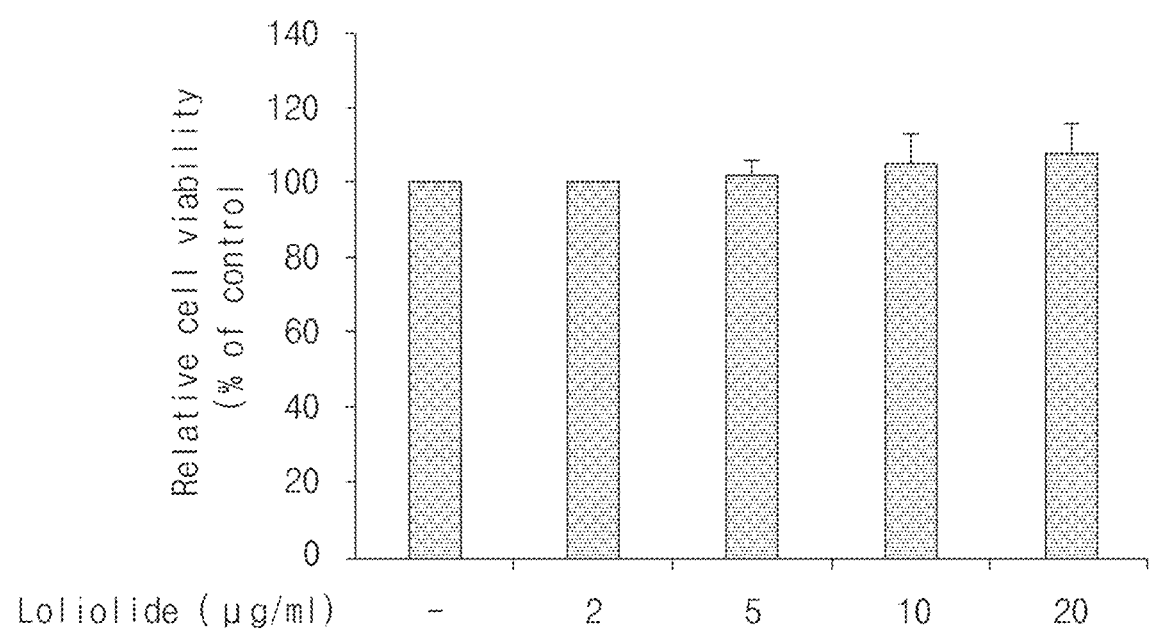
FIG. 8 shows a graph illustrating the results where human dermal fibroblasts were treated with loliolide, which was isolated and purified from *Senedesmus* sp. HS4 microalgae, according to concentration, and the cell viabilities of these cells were measured and compared.

As a result, as can be seen in FIG. 8, although the loliolide was treated up to a concentration of 20 μg/mL, the relative viability of the cells was not decreased compared to the control group which was not treated with loliolide. Accordingly, it was confirmed that the loliolide produced from *Scenedesmus* sp. HS4 was not toxic to human dermal fibroblasts at a concentration up to 20 μg/mL.

[Example 7] Confirmation of Cell Viability Recovery Effect of Loliolide on Human Dermal Fibroblasts with Reduced Cell Viability by UV Irradiation Cells, including human dermal fibroblasts, have a reduced viability when irradiated with UV rays such as UVB. In this regard, it was confirmed how the cell viability changes when the loliolide purified as described above is treated on human dermal fibroblasts followed by irradiation with UVB.

Human dermal fibroblasts cultured in the same manner as in Example 6 were dispensed in a 96-well plate by $4 \times 10^3$ cells/well, and loliolide was treated at concentrations of 2 μg/mL, 5 μg/mL, 10 μg/mL, and 20 μg/mL for 6 hours. Then, the medium was irradiated with UVB at 10 $mJ/cm^2$ and cultured further for 24 hours, and cell viability was measured by performing a WST-1 assay in the same manner as in Example 6.

Figure 9:
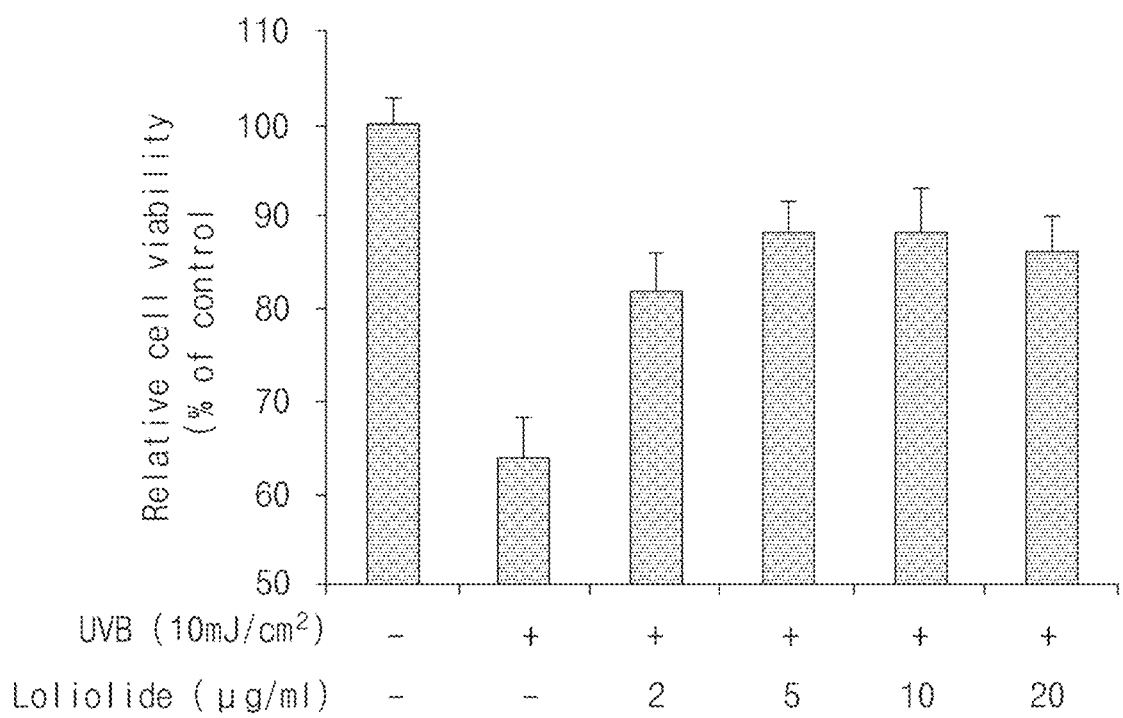
FIG. 9 shows a graph illustrating the results where human dermal fibroblasts irradiated with ultraviolet (UVB) were treated with loliolide, which was isolated and purified from *Senedesmus* sp. HS4 microalgae, according to concentration, and the cell viabilities of these cells were measured and compared, in which the control group was human dermal fibroblasts which were not irradiated with UV light and were not treated with loliolide.

As a result, based on the viability of cells without any treatment as can be seen in FIG. 9, while the control cells which were irradiated with UVB without loliolide treatment showed a decrease in cell viability by 35% to merely reach 65%, the cell viability of the cells treated with loliolide at each concentration was measured to be higher, thereby recovering the cell viability which was decreased by UVB irradiation. The cells in which the recovery effect of cell viability was highest were the cells treated with loliolide at a concentration of 5 μg/mL or 10 μg/mL, in which the cell viability was at a level of 88% to 89%.

In view of the above results, it was confirmed that loliolide has an excellent effect of recovering the cell viability of human dermal fibroblasts reduced by UVB and increasing the cell viability again, and the cell viability was significantly increased compared to the control group even by treatment at 2 μg/mL. Therefore, it was confirmed that the loliolide purified after isolation from *Scenedesmus* sp. HS4 can help the recovery and improvement of skin damaged by light.

[Example 8] Confirmation of Effect of Promoting Expression of Collagen Gene (Col1A1) and Effect of Inhibiting Expression of Collagenase Gene (MMP1) by Loliolide Collagen is one of the main proteins constituting the skin, and a decrease in collagen level can adversely affect the elasticity and moisture of the skin. ColA1, a gene related to collagen synthesis as described above, can be inhibited by irradiation with UV rays (e.g., UVB), and MMP1 gene for collagenase, which is a collagen-decomposing protein, may be increased in expression by UVB irradiation, which may ultimately induce a decrease in the amount of collagen production. In this regard, the changes in expression levels of these genes were measured when treated with loliolide isolated from *Scenedesmus* sp. HS4 and purified.

First, human dermal fibroblasts cultured in the same manner as in Example 6 were dispensed in a 96-well plate in an amount of 4×10$^3$ cells/well, and UVB was irradiated to the medium at 10 mJ/cm$^2$. Then, the medium of the human dermal fibroblasts irradiated with UV rays was treated with loliolide at a concentration of 5 μg/mL and 10 μg/mL, which showed the highest effect of cell viability recovery as in the result of Example 7, and cultured for 24 hours. Thereafter, the changes in expression levels of the ColA1 gene and the MMP1 gene were measured through quantitative real time-PCR (qRT-PCR). During this process, SYBR green I (Invitrogen), which is a fluorescent material, was used to examine the amount of the DNA product amplified by PCR in real time. Specifically, 0.2 μM of the primers prepared with the sequences shown in Table 3 below were added to a PCR tube, and mixed with 50 mM KCl, 20 mM Tris/HCl (pH 8.4), 0.8 mM dNTP, 0.5 U DNA polymerase (Extaq DNA polymerase), 3 mM MgCl$_2$ and 1×SYBR Green I so as to prepare a reaction solution. Then, PCR was performed using a PCR device (Linegene K, BioER, China)(PCR conditions: primary denaturation for 3 minutes, denaturation at 94° C. for 30 seconds, annealing at 58° C. for 30 seconds, and polymerization at 72° C. for 30 seconds, a total of 40 cycles), and the fluorescence intensity was measured for each cycle.

TABLE 3

| SEQ ID NO | Sequence Name | Nucleotide Sequence (5' -> 3') |
|---|---|---|
| 1 | COL1A1 forward primer | AGGGCCAAGACGAAGACATC |
| 2 | COL1A1 reverse primer | AGATCACGTCATCGCACAACA |

TABLE 3-continued

| SEQ ID NO | Sequence Name | Nucleotide Sequence (5' -> 3') |
|---|---|---|
| 3 | MMP1 forward primer | TCTGACGTTGATCCCAGAGAGCAG |
| 4 | MMP1 reverse primer | CAGGGTGACACCAGTGACTGCAC |
| 5 | β-actin forward primer | GGATTCCTATGTGGGCGACGA |
| 6 | β-actin reverse primer | CGCTCGGTGAGGATCTTCATG |

Figure 10:
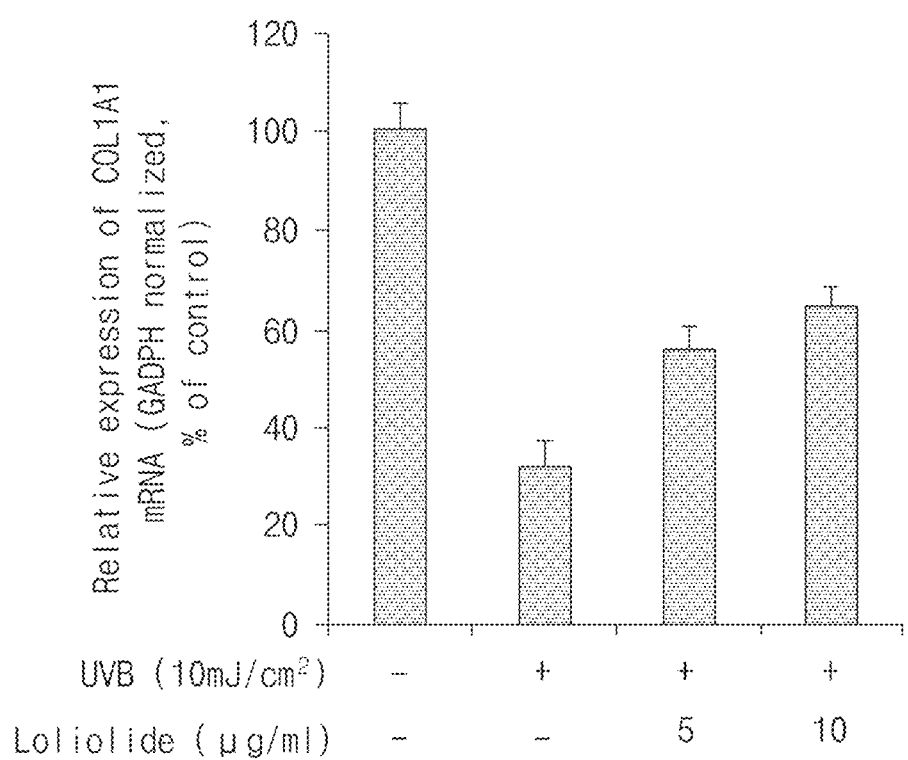
FIG. 10 shows a graph illustrating the results where human dermal fibroblasts irradiated with ultraviolet (UVB) were treated with loliolide, which was isolated and purified from *Senedesmus* sp. HS4 microalgae, according to concentration, and the expression level of the Col1A1 gene expressed in the above cells was measured through qRT-PCR, in which the control group was human dermal fibroblasts which were not irradiated with UV light and were not treated with loliolide.

As a result of the measurement of the expression level of ColA1 gene, based on the expression level of the cells without any treatment as shown in FIG. 10, while the control cells which were not treated with loliolide and irradiated only with UVB showed a decrease in the expression level of ColA1 gene by 70% to merely reach 30%, the expression level of ColA1 gene was measured to be 55% when the cells were treated with loliolide at a concentration of 5 μg/mL, and the expression level of ColA1 gene was measured to be 65% when the cells were treated with loliolide at a concentration of 10 μg/mL, thereby recovering the expression level that was decreased by UVB irradiation.

Figure 11:
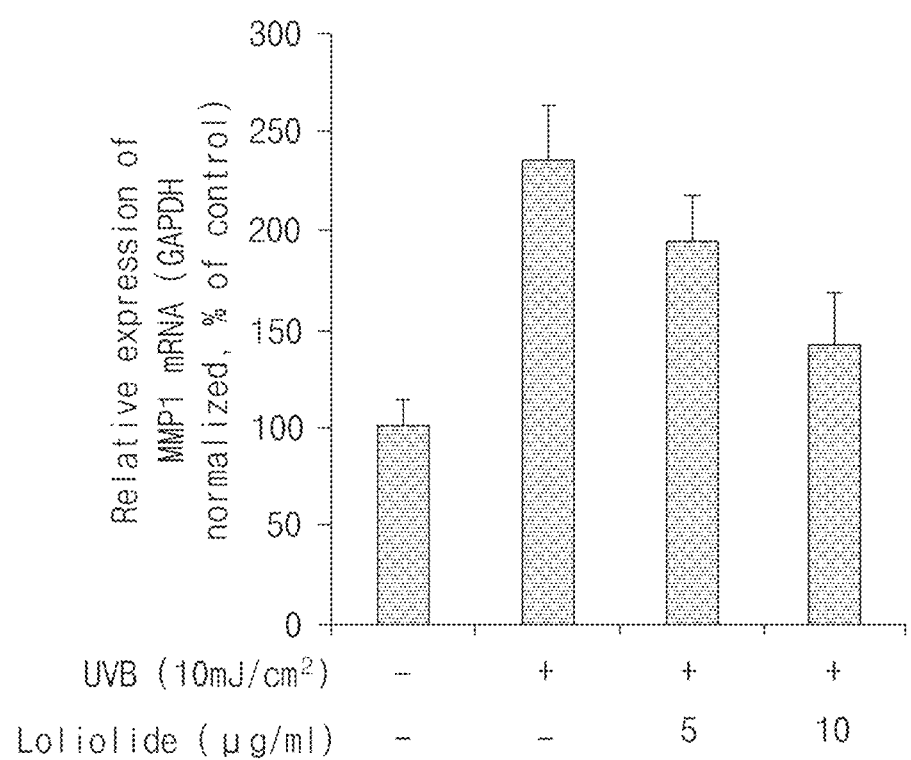
FIG. 11 shows a graph illustrating the results where human dermal fibroblasts irradiated with ultraviolet (UVB) were treated with loliolide, which was isolated and purified from *Senedesmus* sp. HS4 microalgae, according to concentration, and the expression level of the MMP1 gene expressed in the above cells was measured through qRT-PCR, in which the control group was human dermal fibroblasts which were not irradiated with UV light and were not treated with loliolide.

As a result of measuring the expression level of MMP1 gene, based on the expression level of the cells without any treatment as shown in FIG. 11, while the control cells which were irradiated with UVB only and not treated with loliolide, showed a 2.4-fold increase in the gene expression of MMP1 gene, the expression level of MMP1 gene was measured to be 25% when the cells were treated with loliolide at a concentration of 5 μg/mL, and the expression level of MMP1 gene was measured to be 46% when the cells were treated with loliolide at a concentration of 10 μg/mL, thus showing a decrease in expression level.

In view of the above results, it was confirmed that loliolide has an effect of recovering and increasing the expression level of ColA1 gene in human dermal fibroblasts, which was reduced by UVB irradiation, and decreasing the expression level of MMP1 gene expression, thus having the effect of increasing the amount of collagen produced in human dermal fibroblasts. Therefore, it was confirmed that the loliolide purified after isolation from *Scenedesmus* sp. HS4 can help the recovery and improvement of the skin damaged by light and help maintain skin elasticity and moisture In the above, the present invention has been described in detail only with respect to the described embodiments, however, it is apparent to those skilled in the art that various modifications and variations are possible within the scope of the technical spirit of the present invention, and it is natural that such variations and modifications fall within the scope of the appended claims.

(Accession No.)

Depositary: Korea Research Institute of Bioscience and Biotechnology

Accession No: KCTC13784BP

Date of Deposit: Jan. 4, 2019

The invention claimed is:

1. A freeze-dried strain of *Scenedesmus* sp. HS4 deposited under Accession No. KCTC 13784BP, wherein the strain is prepared by culturing *Scenedesmus* sp. JD052 for one month under conditions where an initial light dose is 50 µmol:m−2:s−1 and an initial concentration of glucose is at 0 g/L; culturing for one month under conditions where a light dose is 30 µmol-m−2:s−1 and a concentration of glucose is 0.1 g/L; culturing for one month under conditions where a light dose is 15 µmol-m−2:s−1 and a concentration of glucose is 1 g/L; culturing for one month under conditions where a light dose is 5 µmol:-m−2-s−1 and a concentration of glucose is 5 g/L; and finally culturing for one month under conditions where a light dose is 0 µmol:m−2:s−1 and a concentration of glucose is 10 g/L, and wherein the freeze-dried strain is in the form of an emulsion, a tablet, a capsule, or a gel.

2. The *Scenedesmus* sp. HS4 of claim 1, wherein the *Scenedesmus* sp. HS4 is capable of producing loliolide.

3. A composition comprising a freeze-dried strain of *Scenedesmus* sp. HS4 deposited under Accession No. KCTC 13784BP and an additive, wherein the strain is prepared by culturing *Scenedesmus* sp. JD052 for one month under conditions where an initial light dose is 50 µmol-m−2:s−1 and an initial concentration of glucose is at 0 g/L; culturing for one month under conditions where a light dose is 30 µmol-m−2:s−1 and a concentration of glucose is 0.1 g/L; culturing for one month under conditions where a light dose is 15 µmol-m−2:s−1 and a concentration of glucose is 1 g/L; culturing for one month under conditions where a light dose is 5 µmol-m−2:s−1 and a concentration of glucose is 5 g/L; and finally culturing for one month under conditions where a light dose is 0 µmol:m−2-s−1 and a concentration of glucose is 10 g/L, and wherein the composition is in the form of an emulsion, a tablet, a capsule, or a gel.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: COL1A1 forward primer

<400> SEQUENCE: 1
agggccaaga cgaagacatc                                                    20

<210> SEQ ID NO 2
<211> LENGTH: 21
<212> TYPE: DNA
<213> ORGANISM: Artificial Sequence
<220> FEATURE:
<223> OTHER INFORMATION: COL1A1 reverse primer

<400> SEQUENCE: 2
agatcacgtc atcgcacaac a                                                  21

<210> SEQ ID NO 3
<211> LENGTH: 24
<212> TYPE: DNA
<213> ORGANISM: Artificial Sequence
<220> FEATURE:
<223> OTHER INFORMATION: MMP1 forward primer

<400> SEQUENCE: 3
tctgacgttg atcccagaga gcag                                               24

<210> SEQ ID NO 4
<211> LENGTH: 23
<212> TYPE: DNA
<213> ORGANISM: Artificial Sequence
<220> FEATURE:
<223> OTHER INFORMATION: MMP1 reverse primer

<400> SEQUENCE: 4
cagggtgaca ccagtgactg cac                                                23

<210> SEQ ID NO 5
<211> LENGTH: 21
<212> TYPE: DNA
<213> ORGANISM: Artificial Sequence
<220> FEATURE:
<223> OTHER INFORMATION: beta-actin forward primer

<400> SEQUENCE: 5
ggattcctat gtgggcgacg a                                                  21

<210> SEQ ID NO 6
<211> LENGTH: 21
<212> TYPE: DNA
<213> ORGANISM: Artificial Sequence
<220> FEATURE:
<223> OTHER INFORMATION: beta-actin reverse primer

<400> SEQUENCE: 6
cgctcggtga ggatcttcat g                                                  21